(12) United States Patent
Gonzales, Jr.

(10) Patent No.: US 12,080,431 B1
(45) Date of Patent: *Sep. 3, 2024

(54) METHOD FOR ANALYZING DIAGNOSES, AND DETERMINING AND REPORTING WORKING DIAGNOSIS RELATED DATA USING STANDARDIZED PATIENT MEDICAL INFORMATION

(71) Applicant: Hospitalists Now, Inc., Austin, TX (US)

(72) Inventor: Merced Gonzales, Jr., San Antonio, TX (US)

(73) Assignee: Hospitalists Now, Inc., Austin, TX (US)

( * ) Notice: Subject to any disclaimer, the term of this patent is extended or adjusted under 35 U.S.C. 154(b) by 100 days.

This patent is subject to a terminal disclaimer.

(21) Appl. No.: 17/735,847

(22) Filed: May 3, 2022

Related U.S. Application Data

(63) Continuation of application No. 16/833,546, filed on Mar. 28, 2020, now Pat. No. 11,348,689.

(60) Provisional application No. 62/829,558, filed on Apr. 4, 2019.

(51) Int. Cl.
*G16H 50/20* (2018.01)
*G06F 3/04817* (2022.01)
*G06F 3/0482* (2013.01)
*G16H 10/60* (2018.01)
*G16H 50/30* (2018.01)

(52) U.S. Cl.
CPC ......... *G16H 50/20* (2018.01); *G06F 3/04817* (2013.01); *G06F 3/0482* (2013.01); *G16H 10/60* (2018.01); *G16H 50/30* (2018.01)

(58) Field of Classification Search
CPC ........ G16H 50/20; G16H 10/60; G16H 50/30; G06F 3/04817; G06F 3/0482
See application file for complete search history.

(56) References Cited

U.S. PATENT DOCUMENTS

| | | | |
|---|---|---|---|
| 5,307,262 A | 4/1994 | Ertel | |
| 6,850,252 B1 | 2/2005 | Hoffberg | |
| 7,181,017 B1 | 2/2007 | Nagel et al. | |
| 7,587,368 B2 | 9/2009 | Felsher | |
| 7,590,550 B2 | 9/2009 | Schoenberg | |
| 7,617,078 B2 | 11/2009 | Rao et al. | |
| 7,630,386 B2 | 12/2009 | Herz et al. | |
| 7,653,558 B2 | 1/2010 | Schoenberg | |
| 7,672,858 B2 | 3/2010 | Tolan et al. | |
| 7,689,682 B1 | 3/2010 | Eldering et al. | |
| 7,734,477 B2 | 6/2010 | Bellin et al. | |
| 7,765,114 B2 | 7/2010 | Frick | |

(Continued)

*Primary Examiner* — William L Bashore
*Assistant Examiner* — Gregory A Distefano
(74) *Attorney, Agent, or Firm* — Hemingway & Hansen, LLP; D. Scott Hemingway; Elizabeth P. Hartman

(57) ABSTRACT

A hardware processor-based patient system and method having an indexing and referential storage that collects, converts and consolidates patient diagnosis information into a standardized format, including converting input diagnosis information provided by different sources and different formats into that standardized format, as well as specialized diagnosis entry subprograms to analyze patient diagnosis information, calculate diagnosis specific data and generate a working diagnosis, and display and store the diagnosis specific data and generate a working.

27 Claims, 16 Drawing Sheets

(56) References Cited

U.S. PATENT DOCUMENTS

| | | |
|---|---|---|
| 7,774,215 B2 | 8/2010 | Rosow et al. |
| 7,788,111 B2 | 8/2010 | Haskell et al. |
| 7,801,956 B1 | 9/2010 | Cumberbatch et al. |
| 7,805,377 B2 | 9/2010 | Felsher |
| 7,813,822 B1 | 10/2010 | Hoffberg |
| 7,818,183 B2 | 10/2010 | Schoenberg |
| 7,831,445 B2 | 11/2010 | Reiner |
| 7,835,928 B2 | 11/2010 | Schoenberg |
| 7,840,418 B2 | 11/2010 | Schoenberg |
| 7,848,937 B2 | 12/2010 | Schoenberg |
| 7,853,456 B2 | 12/2010 | Soto et al. |
| 7,865,377 B2 | 1/2011 | Schoenberg |
| 7,890,345 B2 | 2/2011 | Schoenberg |
| 7,890,351 B2 | 2/2011 | Schoenberg |
| 7,895,061 B2 | 2/2011 | Schoenberg |
| 7,912,737 B2 | 3/2011 | Schoenberg |
| 7,933,783 B2 | 4/2011 | Schoenberg |
| 7,937,275 B2 | 5/2011 | Schoenberg |
| 7,945,456 B2 | 5/2011 | Schoenberg |
| 7,966,647 B1 | 6/2011 | Igoe et al. |
| 7,970,827 B1 | 6/2011 | Cumberbatch et al. |
| 7,974,714 B2 | 7/2011 | Hoffbert |
| 8,073,708 B1 | 12/2011 | Igoe et al. |
| 8,209,218 B1 | 6/2012 | Basu et al. |
| 8,666,773 B1 | 3/2014 | Gonzales |
| 10,340,040 B2 * | 7/2019 | Loeb ................. G16H 50/20 |
| 11,183,275 B1 * | 11/2021 | Chan ................. G16H 50/30 |
| 2003/0050794 A1 | 3/2003 | Keck |
| 2003/0158749 A1 | 8/2003 | Olchanski et al. |
| 2004/0064341 A1 | 4/2004 | Langan et al. |
| 2004/0128163 A1 | 7/2004 | Goodman et al. |
| 2005/0177396 A1 | 8/2005 | Gottlieb et al. |
| 2007/0203750 A1 | 8/2007 | Volcheck |
| 2007/0239484 A1 | 10/2007 | Arond et al. |
| 2008/0133269 A1 | 6/2008 | Ching |
| 2008/0133290 A1 | 6/2008 | Siegrist et al. |
| 2008/0154637 A1 | 6/2008 | Capelli et al. |
| 2008/0154642 A1 | 6/2008 | Marble et al. |
| 2008/0243549 A1 | 10/2008 | Woronka et al. |
| 2008/0294507 A1 | 11/2008 | Reiner |
| 2009/0012816 A1 | 1/2009 | Cookson et al. |
| 2009/0024414 A1 | 1/2009 | Mansour et al. |
| 2009/0099865 A1 | 4/2009 | Zak et al. |
| 2009/0182580 A1 | 7/2009 | Martin et al. |
| 2009/0271218 A1 * | 10/2009 | Mok ................. G16H 70/20 705/2 |
| 2009/0281826 A1 | 11/2009 | Zak et al. |
| 2010/0114599 A1 | 5/2010 | Lanning et al. |
| 2010/0169119 A1 | 7/2010 | Hussain |
| 2011/0125531 A1 * | 5/2011 | Seare ................. G06Q 10/00 705/2 |
| 2011/0161857 A1 | 6/2011 | Kramer |
| 2013/0073306 A1 | 3/2013 | Shlain et al. |
| 2013/0297347 A1 * | 11/2013 | Cardoza ................. G06F 16/36 705/3 |
| 2015/0213224 A1 | 7/2015 | Amarasingham |
| 2018/0081859 A1 * | 3/2018 | Snider ................. G06F 40/44 |
| 2018/0301206 A1 * | 10/2018 | Robbins ................. G06Q 30/06 |
| 2020/0227175 A1 * | 7/2020 | Salomon ................. G16H 50/70 |
| 2020/0286600 A1 * | 9/2020 | De Brouwer .......... G16H 50/20 |

* cited by examiner

| Name | BPCI | Patient Class | Room | LOS | GMLOS | Variance |
|---|---|---|---|---|---|---|
| ADAMS, ANN | | | MED-433 | 0 | 0 | 0 |

ADAMS, ANN
PCN: A0362478
MRN: ADAMS364
ASSIGNED MD: SEAN CROWLEY
REF MD: NO PCP.
INSURANCE:
(W) DRG:

[edit]

[launch survey]

| | |
|---|---|
| Ref MD: NO PCP | |
| LOS/GMLOS/VAR | 0/0/0 |
| SOI/ROM | ⚠ |
| DRG Weight | |
| Missing Dx's | 0 |
| RAF/HCC | |
| Missing Charges | ⚠ |

Enter a diagnosis here.

[Import Diagnosis Code(s)] — 401

ICD Helper
[Enter an ICD Keyword]

DRG:
Description:
GMLOS:
Weight:
APR DRG:
APR DRG Description:
Severity of Illness:
Risk of Mortality:

[update] [cancel]

FIG. 4A

| ╬ Name | ╬ BPCI | ╬ Patient Class | ╬ Room | ╬ LOS | ╬ GMLOS | ╬ Variance |
|---|---|---|---|---|---|---|
| ADAMS, ANN | | | MED-433 | 0 | 0 | 0 |

ADAMS, ANN
PCN: A0362478
MRN: ADAMS364
ASSIGNED MD: SEAN CROWLEY
REF MD: NO PCP.
INSURANCE:
(W) DRG:

[edit]

✏ ✗ 🗋 👎 📷

[launch survey]

Ref MD: NO PCP
LOS/GMLOS/VAR    0/0/0
SOI/ROM
DRG Weight
Missing Dx's    ⚠
RAF/HCC    0
Missing Charges    ⚠

Enter a diagnosis here.

╬ [chI_____] — 501    [Import Diagnosis Code(s)]

╬ Chest pain, unspecified "R07.9"
╬ R Chronic obstructive pulmonary disease with (acute) exacerbation "J44.1"
╬ R Acute on chronic systolic (congestive) heart failure "I50.23"
╬ R Chronic obstructive pulmonary disease, unspecified "J44.9"
╬ Chronic atrial fibrillation "I48.2"
╬ R Acute on chronic diastolic (congestive) heart failure "I50.33"
╬ Chronic kidney disease, stage 3 (moderate) "N18.3"
╬ R Heart failure, unspecified "I50.9"
╬ R Major depressive disorder, recurrent severe without psychotic features "F33.2"
╬ Headache "R51"
╬ Transient cerebral ischemic attack, unspecified "G45.9"
╬ Tachycardia, unspecified "R00.0"
╬ Chronic pain syndrome "G89.4"
╬ R Acute and chronic respiratory failure with hypoxia "J96.21"
╬ R Chronic kidney disease, stage 4 (severe) "N18.4"
╬ Acute cholecystitis "K81.0"
╬ Acute bronchitis, unspecified "J20.9"
╬ R Schizophrenia, unspecified "F20.9"
╬ Anemia in chronic kidney disease "D63.1"
╬ R Chronic systolic (congestive) heart failure "I50.22"

```
Enter a diagnosis here.
⇅  chI                                    600
                                          Import Diagnosis Code(s)
⇅  Chest pain, unspecified "R07.9"    611
⇅  R Chronic obstructive pulmonary disease with (acute) exacerbation "J44.1"
⇅  R Acute on chronic systolic (congestive) heart failure "I50.23"
⇅  R Chronic obstructive pulmonary disease, unspecified "J44.9"
⇅  R Chronic atrial fibrillation "I48.2"                               612
⇅  R Acute on chronic diastolic (congestive) heart failure "I50.33"
⇅  Chronic kidney disease, stage 3 (moderate) "N18.3"
⇅  R Heart failure, unspecified "I50.9"                   613
⇅  R Major depressive disorder, recurrent severe without psychotic features "F33.2"
```

FIG. 7

```
Enter a diagnosis here.          701
⇅  Acute on chronic systol   R    702    Import Diagnosis Code(s)
⇅  Cardiac arrhythmia, uns        703    ICD Helper
⇅
⇅                                         Enter an ICD Keyword
⇅
⇅                                         DRG: 293
⇅                                         Description: Heart failure & shock
⇅                                         w/o CC/MCC
⇅                                         GMLOS: 2.4
⇅                                         Weight: 0.6656
⇅                                  704
⇅                                         APR DRG: 194
⇅                                         APR DRG Description: Heart failure
⇅                                         Severity of Illness: 1
⇅                                         Risk of Mortality: 1

[update]   [cancel]
```

FIG. 8A

Enter a diagnosis here.

| Acute on chronic systol | 801 |
| Cardiac arrhythmia, uns | 802 |

DRG: 293 ~ 803
Description: Heart failure & shock w/o CC/MCC ~ 804
GMLOS: 2.4 ~ 805
Weight: 0.6656 ~ 806
APR DRG: 194 ~ 807
APR DRG Description: Heart failure ~ 808
Severity of Illness: 1 ~ 809
Risk of Mortality: 1 ~ 810

Enter a diagnosis here.

| Cardiac arrhythmia, uns | 812 |
| Acute on chronic systol | 811 |

DRG: 308 ~ 813
Description: Cardiac arrhythmia and conduction disorders w MCC
GMLOS: 3.6 ~ 815
Weight: 1.2036 ~ 816
APR DRG: 201 ~ 817
APR DRG Description: Cardiac arrhythmia & conduction disorders
Severity of Illness: 1 ~ 819
Risk of Mortality: 2 ~ 820

| ✛ Name | ⇅ BPCI | ⇅ Patient Class | ⇅ Room | ⇅ LOS | ⇅ GMLOS | ⇅ Variance |
|---|---|---|---|---|---|---|
| ADAMS, ANN | W | | MED-433 | 0 | 3.6 | -3.6 |

ADAMS, ANN
PCN: A0362478
MRN: ADAMS364
ASSIGNED MD: SEAN CROWLEY
REF MD: NO PCP.
INSURANCE:
(W) DRG: 308 Cardiac arrhythmia & conduction disorders w MCC

[edit]

launch survey

| Ref MD: NO PCP | |
| LOS/GMLOS | 0/3.6 |
| Variance | 0 |
| SOI/ROM | 1/2 |
| DRG Weight | 1.2036 |
| Edit Dx's | |
| RAF/HCC | 1 |
| Missing Charges | ⚠ |

Enter a diagnosis here.

⇅ Cardiac arrhythmia, uns — 901
⇅ Acute on chronic systol  (R) — 902

[Import Diagnosis Code(s)]

ICD Helper
[Enter an ICD Keyword]

DRG: 308
Description: Cardiac arrhythmia and conduction disorders w MCC
GMLOS: 3.6 — 904
Weight: 1.2036
APR DRG: 201
APR DRG Description: Cardiac arrhythmia & conduction disorders
Severity of Illness: 1
Risk of Mortality: 2

[update]  [cancel]

| Name | BPCI | Patient Class | Room | LOS | GMLOS | Variance |
|---|---|---|---|---|---|---|
| ADAMS, ANN | W | | MED-433 | 0 | 3.6 | -3.6 |

ADAMS, ANN
PCN: A0362478
MRN: ADAMS364
ASSIGNED MD: SEAN CROWLEY    [edit]
REF MD: NO PCP.
INSURANCE:
(W) DRG: 308 Cardiac arrhythmia & conduction disorders w MCC

[launch survey]

| | |
|---|---|
| Ref MD: NO PCP | |
| LOS/GMLOS | 0/3.6 |
| Variance | 0 |
| SOI/ROM | 1/2 |
| DRG Weight | 1.2036 |
| Edit Dx's | |
| RAF/HCC | 1 |
| Missing Charges | ⚠ |

Risk Adjusted Diagnosis Codes YTD

| ICD10 | HCC Category | First Recorded By | Last Recorded |
|---|---|---|---|
| I50.23 | 85 | Sean Crowley, MD | 2/28/2019 |

| ⊕ Name | ⇅ BPCI | ⇅ Patient Class | ⇅ Room | ⇅ LOS | ⇅ GMLOS | ⇅ Variance |
|---|---|---|---|---|---|---|
| ADAMS, ANN | W | | MED-433 | 0 | 3.6 | -3.6 |
| BARNS, BILL | W | | MED-524 | 2 | 4.2 | -2.2 |

FIG. 11

METHOD FOR ANALYZING DIAGNOSES, AND DETERMINING AND REPORTING WORKING DIAGNOSIS RELATED DATA USING STANDARDIZED PATIENT MEDICAL INFORMATION

RELATED APPLICATION DATA

This application is a continuation of U.S. patent application Ser. No. 16/833,546, filed Mar. 28, 2020, and claims the benefit of U.S. Provisional Application No. 62/829,558, filed Apr. 4, 2019, which is incorporated by reference into this utility patent application.

TECHNICAL FIELD OF THE INVENTION

This invention relates to a method for analyzing, determining and reporting diagnosis related grouping (DRG) codes using standardized patient medical information.

BACKGROUND OF THE INVENTION

Medical records and medical treatment information are often saved in a specialized format on local data processor and storage servers at each particular hospital facility. Thus, while the medical records and medical treatment information in the same hospital facility may have a consistent format throughout that hospital facility, other medical providers, physicians and hospital facilities may use a different format for medical records.

The majority of patients admitted to hospitals have some form of medical coverage, either private medical insurance, or Medicare/Medicaid. Hospitals are reimbursed for medical care directly by the insurer. The present foundation for determining reimbursement to health care facilities by Medicare is diagnosis-related groupings (DRGs). When a patient is admitted to a hospital, the reason for the admission is categorized by one or more DRG codes that are assigned by the health care facility. These DRGs are based on the principal that patients with similar diagnoses would likely spend about the same amount of time as an inpatient and require similar resources while hospitalized. DRGs are how Medicare, Medicaid, and many other health insurance companies categorize hospitalization costs and determine how much to pay for a patient's hospital stay. Rather than paying the hospital for what was actually spent caring for a hospitalized patient, Medicare pays the hospital a fixed amount based on the patient's DRG or diagnosis code. The DRG classification system standardizes prospective payments to hospitals and encourages cost containment initiatives. A DRG payment is generally expected to cover all charges associated with an inpatient stay from patient admission until discharge. The DRG also includes any services provided by outside providers. For these reasons, it is essential to identify and record accurate diagnosis codes, as well as any complications or comorbidities that exist which may affect treatment for the patient.

Crucial data inputs for a hospital or healthcare facility upon admission of a patient include identification and entry of accurate diagnoses and any known comorbidities, along with any appropriate related diagnosis codes, and equally important is updating the diagnosis and diagnosis codes throughout the hospitalization to accurately reflect the resource intensity required for the patient. Treatment for a hospitalized patient is diagnosis-specific as is the allocation of the estimated resources, both labor and non-labor, required during the hospitalization. In medical records, especially in Electronic Medical Records (EMR), diagnoses are assigned unique codes (Diagnosis Related Grouping codes or DRGs), and Working DRGs are defined by Diagnosis Related Groups (DRGs) allocated on admission based on the patient's presenting problem or provisional diagnosis. For DRGs, patients are categorized with respect to diagnosis, treatment, and predicted length of hospital stay. DRGs are assigned based on a number of variables, including: principal diagnosis; secondary diagnosis(es); surgical procedures performed; co-morbidities and complications that may affect treatment; age and sex of the patient; and discharge status. Patients and DRGs are then concurrently reviewed until discharge and diagnoses are edited or updated as needed.

Coding is a major factor in obtaining reimbursement for services as well as maintaining patient records. Coding forms the basis for reimbursement to the healthcare facility by the payer, whether the payer is a government entity, such as Medicare or Medicaid, a private insurer or the patient. Coding diagnoses accurately lets the payer know the extent of the illness or injury of the patient and allows for estimation of resource allocation for treatment. Inaccurate coding of a diagnosis may result in a claim being denied or only be partially covered. As a result, the healthcare facility may not be paid fully for the services provided, or the patient may be unexpectedly responsible for paying out of pocket for the uncovered services.

The length of a patient's hospital stay at a particular hospital facility will depend on the patient's condition and responsiveness to treatment. For every patient's ailment and condition, the patient's insurer will estimate a length of stay in the hospital facility for the purposes of insurance coverage and this estimate is based on the diagnosis as well as how the diagnosis is coded. The patient's stay at the facility may, of course, be extended for medical reasons, such as, if there are delays in the patient's recovery due to post-surgical or other complications. If there are medical reasons for extension of a patient's stay, the expenses incurred during that extended stay are likely to be covered by the patient's insurer. That is, if the patient is not ready medically to be discharged from the hospital facility, the patient's insurer will reimburse the facility for costs associated with a bona fide "medical reason" to extend a patient's hospitalization. For this reason, diagnosis codes need to be reviewed and updated throughout a hospitalization to include the appropriate diagnosis codes for complications or comorbidities.

SUMMARY OF THE INVENTION

The method disclosed herein comprises the steps of entering, via a diagnosis entry subprogram on a hardware data processor patient system, one or more diagnosis for a patient in a health care setting, the one or more diagnosis being a primary diagnosis, and one or more of a secondary diagnosis, a complication diagnosis, or a comorbidity diagnosis, and analyzing, via the diagnosis entry subprogram, the one or more diagnosis in view of the patient's age and sex, discharge status, and any surgical procedures previously performed on the patient. The one or more diagnosis is a primary diagnosis, one or more secondary diagnosis, one or more complication diagnosis, one or more comorbidity diagnosis, or combinations thereof, the one or more diagnosis comprising at least one primary diagnosis.

The method disclosed herein has the steps of calculating, via the diagnosis entry subprogram, diagnosis specific data that includes at least one Diagnosis Related Grouping (DRG) code wherein the diagnosis specific data is calculated based on how the one or more diagnosis was entered in the diagnosis entry subprogram, and generating, via the diagnosis entry subprogram, a working diagnosis from the diagnosis specific data calculated by the diagnosis entry subprogram.

The method disclosed herein has the steps of populating one or more display fields of an electronic medical record (EMR) with the working diagnosis and at least one DRG code generated by the diagnosis entry subprogram, and displaying the working diagnosis and at least some of the diagnosis specific data calculated by the diagnosis entry subprogram; and storing the one or more diagnosis specific data and the working diagnosis generated by the diagnosis entry subprogram in the plurality of non-transitory storage devices programmed with executable instructions using the hardware data processor patient system.

The method disclosed herein further has the steps of calculating one or more modified diagnosis specific data when one or more modified diagnosis is entered via the diagnosis entry subprogram on the hardware data processor patient system, the diagnosis specific data including at least one Diagnosis Related Grouping (DRG) code, and one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating, and generating a modified working diagnosis from the modified diagnosis specific data calculated by the diagnosis entry subprogram.

The method also has the steps of populating one or more display field of the EMR with the modified diagnosis specific data, displaying the modified working diagnosis and the modified diagnosis specific data; and storing the one or more modified diagnosis, the one or more modified diagnosis specific data, and the modified working diagnosis in plurality of non-transitory storage devices programmed with executable instructions using the hardware data processor patient system. The one or more display field of the EMR is one or more display field of a diagnosis quality panel, one or more display field of a patient quality panel, one or more display field of a patient census bar, or combinations thereof.

In the disclosed method, diagnosis specific data further comprises one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating.

In the disclosed method, one or more display field of the EMR is populated with the working diagnosis, the DRG code, and one or more of Diagnosis description, DRG weight, LOS, GMLOS, APR DRG, APR DRG Description, LOS/GMLOS/Variance rating, SOI/ROM, diagnosis status, and RAF/HCC rating. The one or more display field of the EMR is one or more display field of the diagnosis quality panel, one or more display field of the patient quality panel, one or more display field of the patient census bar, or combinations thereof.

In the disclosed method, entering includes manually entering a diagnosis description, selecting a diagnosis description from a menu, importing a diagnosis description from an external source, or manually entering an International Classification of Disease (ICD) number for each of the one or more diagnoses.

In the disclosed method, the EMR shows alerts for missing data, the alert being an alert icon, a change in color, or a combination thereof. The EMR displays color coding, bold text, a leading letter designation, or combinations thereof, with entries for Major Complication or Comorbidity/Complication or Comorbidity (MCC/CC), and risk adjusted diagnoses for rapid visual identification. The diagnosis entry subprogram has customizable abbreviations for DRG codes.

The present invention is a hardware processor-based patient system and method having an indexing and referential storage that collects, converts and consolidates patient information from various physicians and health-care providers and hospital facilities into a standardized format, including converting input medical information, files and treatment information provided by different sources and different formats into that standardized format. Whenever the patient information is updated, the information will first be converted into the standardized format and then stored in the collection of medical records on one or more of the hardware processor-based storage devices. After the updated information about the patient's condition has been stored in the collection, the content server, which is connected to the hardware processor-based storage devices programmed with executable instructions, immediately generates a message containing the updated information about the patient's condition. This message is transmitted in a standardized format over the data processor and storage network to all physicians and health-care providers that have access to the patient's information (e.g., to a medical specialist to review the updated information about the patient's medical condition) so that all users can quickly be notified of any changes without having to manually look up or consolidate all of the providers' updates.

The present invention system and method uses standardization of formatted patient information to provide enhanced performance and increased efficiency over known data processor and storage methods and systems. Patient data from input medical information, files and treatment information is stored in a standardized format in the hardware processor-based patient system and method. Indexing and referential storage and specialized subprograms use hardware processor-based storage devices programmed with executable instructions to collect and consolidate the medical information, files and treatment information provided by different sources and different formats.

The present invention also uses the hardware processor-based patient system and method having an indexing and referential storage and specialized subprograms to receive input of diagnosis data entered by a provider, calculate relevant data based on the entered diagnosis, demographic information, and complications and comorbidities for the patient. The relevant calculated data includes Diagnosis Related Groupings (DRGs), Working DRGs, DRG diagnosis descriptions, Geometric Mean Length of Stay (GMLOS), DRG weights, LOS/GMLOS variance, All Patient Refined (APR) DRGs, APR DRG description, severity of illness (SOI), and risk of mortality (ROM); and provides a display of a working DRG and relevant data determinations in multiple locations on the patient quality screen for access and viewing by the provider. The present invention data storage system and method has enhanced performance and increased efficiency over known data processor and storage methods and systems. The hardware processor-based patient system and method uses indexing and referential storage and specialized subprograms to determine Diagnosis Related Groupings (DRGs) and diagnosis related data calculated from diagnosis data input by a provider in order to ascertain projected resource intensity.

This system supports continuity of care through enhanced communication and notification with relevant clinical and operational providers, and the ability to manage patient medical information, including patient diagnosis and treatment files, using specialized subprograms and indexing and referential storage, which improves the efficiency and performance of hospital information systems by improving and integrating communications. Moreover, the system and method of the present invention allows a hospital facility to take appropriate actions regarding the resource intensity projected for a patient based on calculations of data relevant to the diagnosis entered into the system, and to optimize the input for diagnosis coding.

The present invention is a specialized hardware processor-based system and method, which includes specialized data processor and storage readable medium and subprograms that is not available in a generic computer device, even though a user/provider can access the system through a standard web browser on a computing device or connection to the Internet on a single or multi-tier network. The method provides a graphical user interface (GUI) by a content server, which is hardware or a combination of both hardware and software. A user, such as a health care provider, can be given remote access through the GUI to view or update information about a patient's medical condition using the user's own local device (e.g., a personal data processor and storage or wireless handheld device). When a user wants to update the records, the user can input the update in any format used by the user's local device.

The present invention is a method comprising one or more of the following steps of receiving patient diagnosis information describing a patient's medical condition, including a primary diagnosis, and any existing secondary diagnoses, comorbidities or complications; calculating diagnosis specific related data including DRGs; converting the patient diagnosis information into a standardized data format using a hardware data processor coupled to a plurality of non-transitory storage devices programmed with executable instructions; storing the patient diagnosis information in the standardized format in one or more of the plurality of non-transitory storage devices programmed with executable instructions using the hardware data processor from the patient diagnosis information stored in the plurality of non-transitory storage devices; and displaying diagnosis related data in one or more location of an EMR.

Moreover, the present invention is a method having one or more of the following steps of converting said modified patient diagnosis information into said standardized data format using said hardware data processor coupled to said plurality of non-transitory storage devices if, as determined by said hardware data processor, that there is a sufficient difference in the modified patient diagnosis compared to the patient information stored in said plurality of non-transitory storage devices; storing said modified patient diagnosis information in said standardized format in one or more of said plurality of non-transitory storage devices using said hardware data processor if, as determined by said hardware data processor, that there is a sufficient difference in the modified patient diagnosis information compared to the patient information stored in said plurality of non-transitory storage devices; and, transmitting electronic communications to one or more users about said modified patient diagnosis information stored in said standardized format in one or more of said plurality of non-transitory storage devices.

Additionally, the present invention is a method including one or more of the following steps of determining, by said hardware data processor, the resource intensity projected for a specific patient based on analysis specific to a diagnosis, wherein the diagnosis is entered by manually inputting a diagnosis description or known diagnosis code, selecting a diagnosis code from a dropdown menu auto-filled based on user-entered reference characters or customized abbreviations, or importing diagnosis codes from an existing electronic medical record (EMR); calculating diagnosis specific relevant data, including Diagnosis Related Groupings (DRGs), DRG diagnosis descriptions, Geometric Mean Length of Stay (GMLOS), DRG weights, LOS/GMLOS variance, All Patient Refined (APR) DRGs, APR DRG description, severity of illness (SOI), and risk of mortality (ROM); and providing a display of a working DRG and relevant data determinations in multiple locations and formats in real-time on a patient quality screen of a hospital information system.

Compliance with 35 USC § 101 (Post-Alice) Analysis

The present invention complies with the 35 USC § 101 (utility) requirements for patentable subject matter under the current multi-step analysis. Under Step 1 of the USPTO statutory subject matter analysis (post-Alice), it is shown that the present invention satisfies the "Statutory Category" requirement because the claimed invention is an improved system and method that recites components or a series of steps.

Under Step 2A of Prong 2 of the statutory subject matter analysis (post-Alice), the present invention is not simply a "judicial exception" under 35 USC § 101 because the claimed invention is directed to enhancing the performance and efficiency of a data processor and storage system and network through the conversion and storage of standardized formatted patient information from input medical information, diagnoses, files and treatment information in the hardware processor-based patient system and method and the use of an indexing and referential storage and specialized subprograms that uses hardware processor-based storage devices to collect and consolidate medical information, diagnoses, files and treatment information provided by different sources and different formats. Moreover, the present invention uses indexing and referential storage and specialized subprograms to provide analysis specific to a diagnosis, wherein the diagnosis is entered by manually inputting a diagnosis description or known diagnosis code, selecting a diagnosis code from a dropdown menu auto-filled based on user-entered reference characters or customized abbreviations, or importing diagnosis codes from an existing electronic medical record (EMR); calculates by a specialized subprogram the diagnosis specific values based on the diagnosis input, including Diagnosis Related Groupings (DRGs), DRG diagnosis descriptions, Geometric Mean Length of Stay (GMLOS), DRG weights, LOS/GMLOS variance, All Patient Refined (APR) DRGs, APR DRG description, severity of illness (SOI), and risk of mortality (ROM); and displays a working DRG and relevant diagnosis specific data determinations in multiple locations and formats in real-time on a patient quality screen of a hospital information system. Because the present invention is not an abstract concept, a fundamental economic practice, a method of organizing human activity, an idea (standing alone), or a mathematical relationship, the present invention is not an abstract idea and is not simply a "judicial exception" under Step 2A of Prong 2 of the statutory subject matter 35 USC § 101 analysis (post-Alice).

Even if one were to examine whether Step 2B of Prong 2 of the statutory subject matter analysis (post-Alice) were satisfied (which is not necessary based on the above), the present invention complies with the "Integrated into a Practical Application" requirement under the 35 USC § 101 analysis (post-Alice) because the claimed invention recites a combination of additional elements including storing information in a centralized repository server, providing remote access over a network to a centralized web-based server, converting updated patient information, medical files and diagnosis information that was input by a user in a non-standardized form into a standardized format, automatically updating the system with the diagnosis descriptions or codes input by the user, calculating relevant diagnosis specific data based on the input of one or more diagnosis, any existing complications or comorbidities, and existing demographic information; and auto-populating multiple display fields with the calculated data relevant to the diagnosis, as well as detecting missing diagnosis data, alerting users to missing data, and automatically recalculating data relevant to the diagnosis if the diagnosis input is edited or if additional diagnoses, complications or comorbidities are input, thereby providing healthcare facilities with detailed information about the resource intensity projected for a specific patient.

With these above-identified "additional elements," the claimed invention as a whole integrates the method into a practical application (e.g. Example 41 and 42 from PTAB Subject Matter Eligibility Examples, p. 14-20); and, specifically, the additional elements set forth above recite specific improvements over prior art systems and methods by allowing users to input diagnosis data via several avenues including direct manual entry, selection of matching options, and import of data from another electronic record, allowing users to view in real time the input diagnosis, the relevant data calculated about an initial diagnosis or an updated diagnosis, where the relevant data is calculated based on an entered diagnosis or combination of diagnoses, as well as demographic information in the medical record, and populating the relevant data to display fields on the patient quality screen.

Thus, the claim is eligible because it is not directed to the recited judicial exception of an abstract idea. As noted previously, the claim as a whole does not merely describe generally a method of organizing human activity. But, even when viewed as a whole, the claim adds significantly more (i.e., an inventive concept) to any generalized method. The claimed invention as a whole does not merely describe how to generally "apply" the concept of storing and updating patient information in a data processor and storage environment; and, the claimed data processor and storage components are not recited at a high level of generality; and, the claimed components are not merely invoked as tools to perform an existing medical records update process. Accordingly, this invention is not simply implementing an abstract idea on a generic computer, but even if viewed as a generalized method, the claimed invention includes additional elements that make the claimed invention a practical application. For these reasons, the present invention complies with the 35 USC § 101 (utility) requirements for patentable subject matter under the current multi-step analysis.

Hospitals and other health-care facilities will be reimbursed by Medicare or other insurers for a set amount associated with the DRG codes for a patient's treatment. If a hospital treats a patient while spending less than the prospective DRG payment, it makes a profit. However, if a hospital spends more than the prospective DRG payment treating a patient, it has a loss. Assigning accurate diagnosis codes, which encompass any secondary diagnoses, complications or comorbidities, is therefore essential for all hospitals and healthcare facilities, not only for the purpose of receiving appropriate reimbursement for services rendered, but also, in order to accommodate new patients, allocate resources, including personnel, and deliver healthcare effectively and efficiently. A system and method is needed to accurately record, analyze and report Working Diagnosis Related Groups, identify accurate diagnoses and analyze diagnosis codes to determine relevant diagnosis data, in order to improve patient care, increase overall hospital efficiency and decrease revenue

BRIEF DESCRIPTION OF THE DRAWINGS

FIG. 4A shows an option field on the diagnosis page to import diagnosis codes from an EMR.

FIG. 5 shows a dropdown menu of diagnoses generated by typing in the entry field.

FIG. 6E shows a presentation of Standard ICD codes with no CC.

FIG. 7 shows a Diagnosis screen with updated Dx codes.

FIGS. 8A and 8B show GMLOS as calculated with differently ordered Dx codes.

FIG. 9 shows the display of the relevant Working DRG data.

FIG. 10 shows the Risk Adjustment Factor display screen.

FIG. 11 shows the collapsed quality panel with the saved data.

The objects and features of the invention will become more readily understood from the following detailed description and appended claims when read in conjunction with the accompanying drawings in which like numerals represent like elements.

DETAILED DESCRIPTION OF THE PREFERRED EMBODIMENTS

Figure 1:
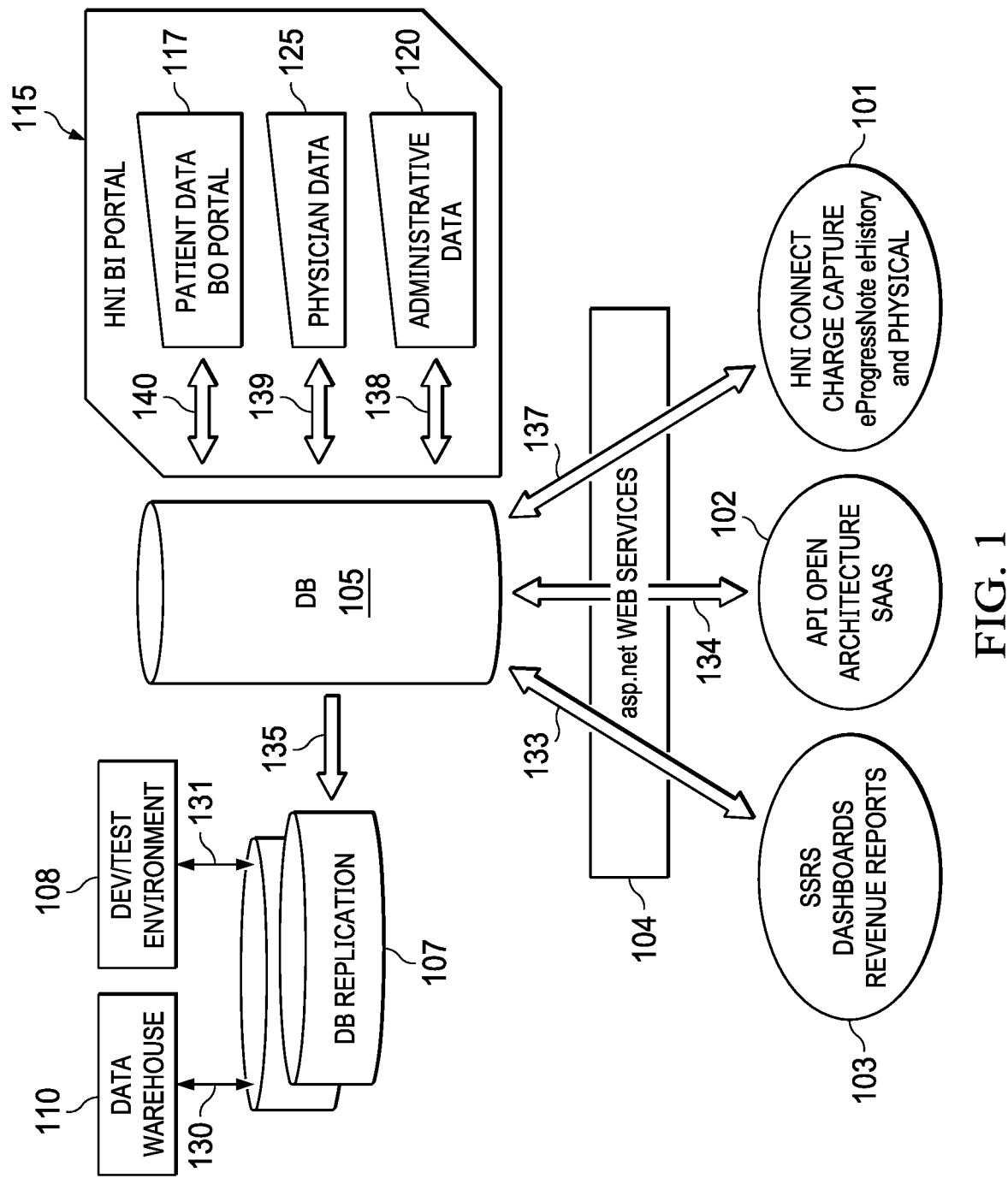
FIG. 1 shows a view of a system for hospital data in accordance with the present invention.

FIG. 1 shows the specialized architecture and storage connections and interaction used in the present invention. The primary storage 105 is coupled to a replication storage 107 through communication link 135. Replication storage 107 is coupled to the data warehouse 110 through communication link 130, and replication storage 107 is coupled to development/test environment protocols 108 through communication link 131.

The primary storage 105 is coupled to SQL Server Reporting Services (SSRS) services protocols 103 through communication link 133 through asp.net webservices support 104. The SSRS services protocols 103 support the "dashboards" and "revenue report" functions. The primary storage 105 is coupled to Application Programing Interface (API) services protocols 102 through communication link 134 through asp.net webservices support 104. The API services protocols 102 support the communication with open architecture protocols and Software as a Service (SAAS) protocols.

The method disclosed herein comprises the steps of entering, via a diagnosis entry subprogram on a hardware data processor patient system, one or more diagnosis for a patient in a health care setting, the one or more diagnosis being a primary diagnosis, and one or more of a secondary diagnosis, a complication diagnosis, or a comorbidity diagnosis, and analyzing, via the diagnosis entry subprogram, the one or more diagnosis in view of the patient's age and sex, discharge status, and any surgical procedures previously performed on the patient. The one or more diagnosis is a primary diagnosis, one or more secondary diagnosis, one or more complication diagnosis, one or more comorbidity diagnosis, or combinations thereof, the one or more diagnosis comprising at least one primary diagnosis.

The method disclosed herein has the steps of calculating, via the diagnosis entry subprogram, diagnosis specific data that includes at least one Diagnosis Related Grouping (DRG) code wherein the diagnosis specific data is calculated based on how the one or more diagnosis was entered in the diagnosis entry subprogram, and generating, via the diagnosis entry subprogram, a working diagnosis from the diagnosis specific data calculated by the diagnosis entry subprogram. The method disclosed herein has the steps of populating one or more display fields of an electronic medical record (EMR) with the working diagnosis and at least one DRG code generated by the diagnosis entry subprogram, and displaying the working diagnosis and at least some of the diagnosis specific data calculated by the diagnosis entry subprogram; and storing the one or more diagnosis specific data and the working diagnosis generated by the diagnosis entry subprogram in the plurality of non-transitory storage devices programmed with executable instructions using the hardware data processor patient system.

The method disclosed herein further has the steps of calculating one or more modified diagnosis specific data when one or more modified diagnosis is entered via the diagnosis entry subprogram on the hardware data processor patient system, the diagnosis specific data including at least one Diagnosis Related Grouping (DRG) code, and one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating, and generating a modified working diagnosis from the modified diagnosis specific data calculated by the diagnosis entry subprogram. The method also has the steps of populating one or more display field of the EMR with the modified diagnosis specific data, displaying the modified working diagnosis and the modified diagnosis specific data; and storing the one or more modified diagnosis, the one or more modified diagnosis specific data, and the modified working diagnosis in plurality of non-transitory storage devices programmed with executable instructions using the hardware data processor patient system. The one or more display field of the EMR is one or more display field of a diagnosis quality panel, one or more display field of a patient quality panel, one or more display field of a patient census bar, or combinations thereof.

In the disclosed method, diagnosis specific data further comprises one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating. In the disclosed method, one or more display field of the EMR is populated with the working diagnosis, the DRG code, and one or more of Diagnosis description, DRG weight, LOS, GMLOS, APR DRG, APR DRG Description, LOS/GMLOS/Variance rating, SOI/ROM, diagnosis status, and RAF/HCC rating. The one or more display field of the EMR is one or more display field of the diagnosis quality panel, one or more display field of the patient quality panel, one or more display field of the patient census bar, or combinations thereof.

In the disclosed method, entering includes manually entering a diagnosis description, selecting a diagnosis description from a menu, importing a diagnosis description from an external source, or manually entering an International Classification of Disease (ICD) number for each of the one or more diagnoses. In the disclosed method, the EMR shows alerts for missing data, the alert being an alert icon, a change in color, or a combination thereof. The EMR displays color coding, bold text, a leading letter designation, or combinations thereof, with entries for Major Complication or Comorbidity/Complication or Comorbidity (MCC/CC), and risk adjusted diagnoses for rapid visual identification. The diagnosis entry subprogram has customizable abbreviations for DRG codes.

Disclosed herein is a method comprising the steps of entering, via a diagnosis entry subprogram on a hardware data processor patient system, one or more diagnosis for a patient in a health care setting, said one or more diagnosis being one or more of a primary diagnosis, one or more secondary diagnosis, one or more complication diagnosis, or one or more comorbidity diagnosis, wherein said one or more diagnosis comprises at least one primary diagnosis, said entering being manually entering a diagnosis description, selecting a diagnosis description from a menu, importing a diagnosis description from an external source, or manually entering an International Classification of Disease (ICD) number for each of said one or more diagnosis; converting said one or more diagnosis into a standardized data format using said hardware data processor patient system coupled to a plurality of non-transitory storage devices programmed with executable instructions; and storing, via indexing and referential storage, said one or more diagnosis in said standardized format in one or more of said plurality of non-transitory storage devices using said hardware data processor patient system.

The method as disclosed herein has the steps of analyzing, via the diagnosis entry subprogram, said one or more diagnosis in view of the patient's age and sex, discharge status, and any surgical procedures performed; calculating, via the diagnosis entry subprogram, diagnosis specific data, said diagnosis specific data including at least one Diagnosis Related Grouping (DRG) code wherein the diagnosis specific data is calculated based on the order said one or more diagnosis is entered in said diagnosis entry subprogram; and generating, via the diagnosis entry subprogram, a working diagnosis from the diagnosis specific data calculated by the diagnosis entry subprogram. The method as disclosed herein has the steps of populating one or more display fields in a diagnosis quality panel of an electronic medical record (EMR) with the working diagnosis and at least one DRG code generated by the diagnosis entry subprogram, populating one or more display fields in a patient quality panel of an electronic medical record (EMR) with the working diagnosis and at least one DRG code generated by the diagnosis entry subprogram; populating one or more fields of a patient census bar of the EMR with one or more of said diagnosis specific data generated by the diagnosis entry subprogram; and displaying in real-time the working diagnosis and diagnosis specific data generated from said diagnosis data entered therein; and storing, via indexing and referential storage, said one or more diagnosis specific data and said working diagnosis generated by said diagnosis entry subprogram, in said standardized format in one or more of said plurality of non-transitory storage devices programmed with executable instructions using said hardware data processor patient system.

The method disclosed herein further has the steps of calculating one or more modified diagnosis specific data when one or more modified diagnosis is entered via the diagnosis entry subprogram on the hardware data processor patient system, said diagnosis specific data including at least one Diagnosis Related Grouping (DRG) code, and one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating; generating a modified working diagnosis from the modified diagnosis specific data calculated by the diagnosis entry subprogram; populating the diagnosis panel, the patient quality panel and the patient census bar of the EMR with the modified diagnosis specific data; displaying in real time, the modified working diagnosis and modified diagnosis specific data; and storing, via indexing and referential storage, said one or more modified diagnosis, said one or more modified diagnosis specific data, and said modified working diagnosis in said standardized format in one or more of said plurality of non-transitory storage devices programmed with executable instructions using said hardware data processor patient system. The diagnosis specific data further comprises one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating.

In the disclosed method the diagnosis quality panel of the EMR is populated with the working diagnosis, the DRG code, and one or more of Diagnosis description, DRG weight, LOS, GMLOS, APR DRG, APR DRG Description, LOS/GMLOS/Variance rating, SOI/ROM, diagnosis status, and RAF/HCC rating; the patient quality panel of the EMR is populated with the working diagnosis, the DRG code, and one or more of Diagnosis description, DRG weight, LOS, GMLOS, APR DRG, APR DRG Description, LOS/GMLOS/Variance rating, SOI/ROM, diagnosis status, and RAF/HCC rating; and the patient census bar of the EMR is populated with one or more of said working diagnosis, DRG code, Diagnosis description, DRG weight, LOS, GMLOS, APR DRG, APR DRG Description, LOS/GMLOS/Variance rating, SOI/ROM, diagnosis status, and RAF/HCC rating. The diagnosis quality panel shows alerts for missing data, said alert being an alert icon, a change in color, or a combination thereof; the diagnosis quality panel displays color coding, bold text, a leading letter designation, or combinations thereof, with entries for Major Complication or Comorbidity/Complication or Comorbidity (MCC/CC), and risk adjusted diagnoses for rapid visual identification; and the diagnosis entry subprogram has customizable abbreviations for DRG codes.

The present invention uses the hardware processor-based patient system and method shown in FIG. 1, which has an indexing and referential storage that collects, converts and consolidates patient information from various physicians and health-care providers and hospital facilities into a standardized format, including converting input diagnosis, medical information, files and treatment information provided by different sources and different formats into that standardized format. Whenever the patient diagnosis or information is updated, it will first be converted into the standardized format and then stored in the collection of medical records on one or more of the hardware processor-based storage devices. After the updated information about the patient's condition has been stored in the collection, the content server, which is connected to the hardware processor-based storage devices, immediately generates a message containing the updated information about the patient's condition. This message is transmitted in a standardized format over the data processor and storage network to all physicians and health-care providers that have access to the patient's information (e.g., to a medical specialist to review the updated information about the patient's medical condition) so that all users can quickly be notified of any changes without having to manually look up or consolidate all of the providers' updates.

This present invention ensures that health care providers and hospital facilities are notified and have access to changes in the patient's diagnosis or status so they can readily adapt their own medical diagnostic and treatment strategy in accordance with other providers' actions. The message can be in the form of an email message, text message, or other type of message known in the art. The present invention file data storage system and method, as well as the standardization of formatted patient information, enhances the performance and increases the efficiency of the present invention over known data processor and storage methods and systems through the storage of standardized formatted patient information from input medical information, files and treatment information in the hardware processor-based patient system and method and the use of indexing and referential storage and specialized subprograms that uses hardware processor-based storage devices to collect and consolidate medical information, diagnoses, files and treatment information provided by different sources and different formats.

The API shown in FIG. 1 is initialized and runs a specialized program periodically to receive information from a hospital or customer facility. For example, the API code can be executed every 30 minutes to check if any new data has been received from a hospital or customer facility. If data has been received during that period of time, the API program will accumulate the received data and push it into the proper storage entries associated with the facility that transferred the data to the data processor and storage software used in the present system. Alternatively, the API subprogram on the system may reach out to certain hospital or customer facilities that provide access to their storage system so that the API subprogram can capture data from the hospital or customer facility data processor and storage system for uploading to the data to the data processor and storage software used in the present system.

The present invention shown in FIG. 1 is a specialized system and method, which includes specialized data processor and storage readable medium and subprograms that are not available in a generic computer device, even though a user/provider accesses the system through a standard web browser on a computing device or connection to the Internet or single or multi-tier network. Also, the present invention works with multiple hospital information systems (HIS), Electronic Medical Record (EMR) systems, administrative data systems, and financial accounting systems. The method provides a graphical user interface (GUI) by a content server, which is hardware or a combination of both hardware and software. A user, such as a health care provider, can be given remote access through the GUI to view or update information about a patient's medical condition or diagnosis using the user's own local device (e.g., a personal data processor and storage or wireless handheld device). When a user wants to update the records, the user can input the update in any format used by the user's local device.

As shown in FIG. 1, the data uploaded onto the storage 105 is formatted in a normalized manner with baseline data fields that include: visit number (encounter number), medical record number, patient name, diagnosis codes, gender (male/female), age (DOB), admission date, assigned doctor, location/department of facility patient admitted to. The demographics data for the patient is also placed in a normalized format of data fields that include: name of patient (first, middle, last name), visit number, medical record number, date of admission, contact address (home, permanent work or work addresses), insurance information (primary insurer: Medicare, Medicaid, BC/BS, secondary insurer: AFLAC, AARP, tertiary insurer: self, employer), parent/guardian information (if patient is minor), social security number (guarantor and patient). The insurance demographic information includes the policy number, group number, and insurance address for each insurer. Upon admission the baseline and demographic information for that patient is input into the storage 105, and the patient information may be accessed from, or input into, the data processor and storage system using a desktop data processor and storage device, mobile phone, intelligent pad devices, or other personal communication device.

The primary storage 105 of FIG. 1 is coupled to services protocols 101 through communication link 137 through asp.net webservices support 104. The services protocols 101 support the invention services for Charge Capture, eProgress Notes, and eHistory & Physical functional protocols. The primary storage 105 is coupled to three portals in the HNI B1 Portal 115, with the primary storage 105 being coupled to Patient Data BO Portal 117 through communication link 140, and the primary storage 105 being coupled to Physician Data 125 protocols through communication link 139, and the primary storage 105 also being coupled to Administrative Data protocol 120 through communication link 138.

Whenever the patient diagnosis or information is updated, it will first be converted into the standardized format and then stored in the collection of medical records on one or more of the hardware processor-based storage devices. After the updated information about the patient's diagnosis or condition has been stored in the collection, the content server, which is connected to the hardware processor-based storage devices programmed with executable instructions, immediately generates a message containing the updated information about the patient's diagnosis or condition. This message is transmitted in a standardized format over the data processor and storage network to all physicians and healthcare providers that have access to the patient's information (e.g., to a medical specialist to review the updated information about the patient's medical condition) so that all users can quickly be notified of any changes without having to manually look up or consolidate all of the providers' updates. This ensures that each of a group of health care providers is always given immediate notice and access to changes so they can readily adapt their own medical diagnostic and treatment strategy in accordance with other providers' actions. The message can be in the form of an email message, text message, or other type of message known in the art.

The present invention also shows the hardware processor-based patient system and method having an indexing and referential storage and specialized subprograms to receive input of diagnosis data entered by a provider, calculate relevant data based on the entered diagnosis, demographic information, and complications and comorbidities for the patient, the relevant calculated data including Diagnosis Related Groupings (DRGs), Working DRGs, DRG diagnosis descriptions, Geometric Mean Length of Stay (GMLOS), DRG weights, LOS/GMLOS variance, All Patient Refined (APR) DRGs, APR DRG description, severity of illness (SOI), and risk of mortality (ROM); and providing a display of a working DRG and relevant data determinations in multiple locations on the patient quality screen for access and viewing by the provider. The present invention data storage system and method using a hardware processor enhances the performance and increases the efficiency of the present data processor and storage system over known data processor and storage methods and systems by the use of indexing and referential storage and specialized subprograms to determine Diagnosis Related Groupings (DRGs) and diagnosis related data from diagnosis data input by a provider in order to ascertain projected resource intensity required for treatment.

This system supports continuity of care through enhanced communication and notification with relevant clinical and operational providers, and the ability to manage patient and treatment files and patient diagnosis and medical information using specialized subprograms and indexing and referential storage to improve the efficiency and performance of hospital information systems by improving and integrating communications. Moreover, the system and method of the present invention allows a hospital facility to take appropriate actions regarding the resource intensity projected for a patient based on calculations of data relevant to the diagnosis entered into the system, and to optimize the input for diagnosis coding.

The present invention is a specialized hardware processor-based system and method, which includes specialized data processor and storage readable medium and subprograms that are not available in a generic computer device, even though a user/provider accesses the system through a standard web browser on a computing device or connection to the Internet or single or multi-tier network. The method provides a graphical user interface (GUI) by a content server, which is hardware or a combination of both hardware and software. A user, such as a health care provider, can be given remote access through the GUI to view or update information about a patient's medical condition using the user's own local device (e.g., a personal data processor and storage or wireless handheld device). When a user wants to update the records, the user can input the update in any format used by the user's local device.

The present invention stores data in a more efficient and effective manner than previously used in other data storage systems through the use of an enhanced performance data storage sub-system using a self-referential, indexed data storage protocol and procedure that store all entity types in a single table after indexing is performed to prevent the creation of duplicative data entries in the data storage sub-system. The indexing protocols and procedures used in the enhanced data storage sub-system of the present invention reviews input data (received in health level 7 or HL7 format), and, before the creation of a new record in the data storage sub-system, the enhanced data storage sub-system of present invention using a self-referential, indexed data storage protocol and procedure searches existing records in the data storage sub-system to determine if the patient whose data is being reviewed was previously admitted into a particular hospital facility, a surrounding hospital facility, or any other related hospital facility connected to the present invention system.

If the enhanced data storage sub-system of present invention using a self-referential, indexed data storage protocol and procedure determines that the patient's data being reviewed relates to a patient that was previously admitted into a particular hospital facility, a surrounding hospital facility, or any other related hospital facility connected to the present invention system, then no new record for the patient is created in the data storage system and the input data is directed to the previously created record for that patient. If the enhanced data storage sub-system of the present invention using a self-referential, indexed data storage protocol and procedure determines that the patient's data being reviewed does not relate to a patient that was previously admitted into a particular hospital facility, a surrounding hospital facility, or any other related hospital facility connected to the present invention system, then a new record for the patient is created in the data storage system and the input data is directed to this new record for that patient.

A new record for a patient is only created when it is necessary, and when that patient has not been previously admitted into a particular hospital facility, a surrounding hospital facility, or any other related hospital facility connected to the present invention system. If the new data received for a patient relates to a patient that was previously admitted into a particular hospital facility, a surrounding hospital facility, or any other related hospital facility connected to the present invention system, no new patient record is created and the input data is directed to the previously created records in the data storage system. The avoidance and elimination of duplicate records creation for patients that were previously admitted into a particular hospital facility, a surrounding hospital facility, or any other related hospital facility connected to the present invention system results in a greater efficiency and effectiveness in the storage of patient records than has been previously known in the prior art data storage systems.

The present invention uses of an enhanced performance data storage sub-system having a self-referential, indexed data storage protocol and procedure that supports record storage in a table after indexing, which also allows for faster searching of data stored therein compared to other data storage systems. Moreover, the enhanced performance data storage sub-system using a self-referential, indexed data storage protocol and procedure in the present invention allows for more effective storage of data than other data storage systems, such as image and unstructured data storage. And, the enhanced performance data storage sub-system using a self-referential, indexed data storage protocol and procedure in the present invention provides for more flexibility in the configuration of the data and records stored therein over other data storage systems.

Figure 2:
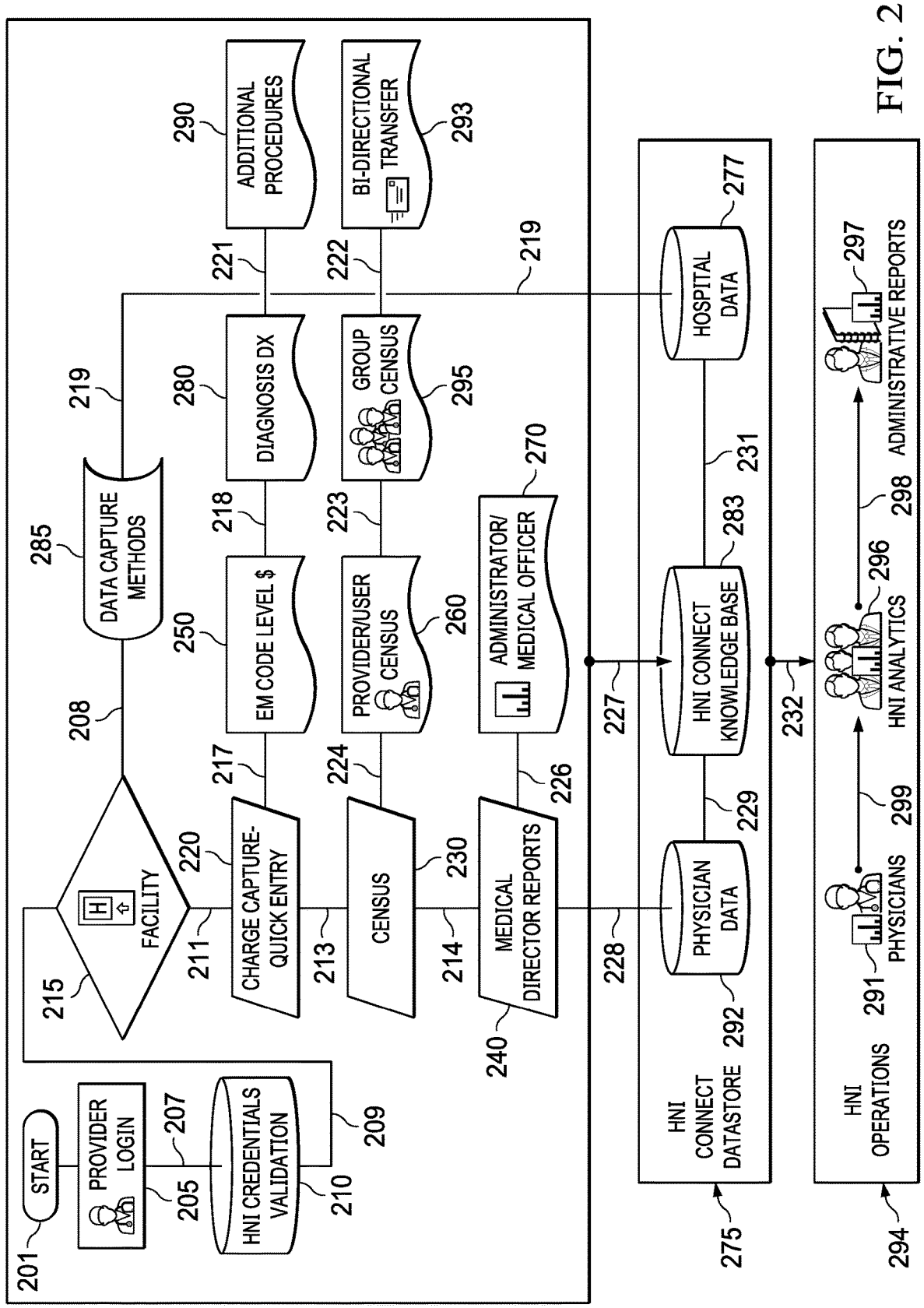
FIG. 2 shows a view of a system data architecture useful for the present invention.

FIG. 2 shows the basic elements of the systems, how it interfaces with external data sources, such as the EMR and HIS systems and data elements associated with inpatient care. Through the present invention's data model, the system enables and integrates data from different types of systems in a fast, flexible, seamless manner. A software control program runs an on demand or by scheduler software routine to check a pre-defined directory that includes data either received or pulled down from different customer hospital systems coupled to the system. The software program starts by asking for a User Login, which must be correctly given to proceed in the program. After the User Login is given to the software program, the software program determines the User's rights and privileges in the next step of the software control program.

By rights and privileges, the type of information that defines such rights and privileges includes: (1) the type of user (e.g. doctor, biller, office manager, admin/executive, physical assistant/nurse practitioner; (2) facilities the User has privileges to (e.g. name of facilities, hospitals, etc. where User works or can access information about patients, hospitalists, assistants, etc.); and (3) the type of facility that User works at or can access information about patients, hospitalists, assistants, etc. (hospital, long term care, nursing home, assisted living facility, rehabilitation facility, skilled nursing facility, etc.).

After the User's rights and privileges are determined, the software control program proceeds to the Home Screen 101 shown in FIG. 1 where the User can access several options, including the Census sub-program, Charge Capture sub-program, eProgress Notes sub-program, eHistory and Physical subprogram, the Changes sub-program, or the Statistics sub-program (SSRS). From the Home Screen 101 and if the User's rights and privileges permit, the User can access facility-based information including the following: (1) the type of facility that User works at or can access information about patients, hospitalists, assistants, etc. (hospital, long term care, nursing home, assisted living facility, rehabilitation facility, skilled nursing facility, etc.); (2) identification of the User's patients such as patient name, room location, demographic information (age, primary address, etc.); and (3) clinical information for each patient (primary diagnosis). This information may be accessed from, or input into, the data processor and storage system using a desktop data processor and storage device, mobile phone, intelligent pad devices, or other personal communication device.

From the Home Screen 101 and if the User's rights and privileges permit, the User may also input information regarding a patient such as the patient clinical history, diagnosis, treatment(s) received, medications (type and dosage), test results, x-rays or scan results, physical examination records, physician notes, lab results, prescription history. The patient prescription history would include drugs prescribed, dosages prescribed, and frequency of dosage, and this prescription history and present prescription types, amounts, and dosages can be shown graphically in the graphical formats shown in FIG. 16, and the software control program can analyze whether the current prescriptions for a particular patient are comparable to, greater than or less than a metric benchmark for similarly-situated patients.

The patient's physical and clinical history can be input or reviewed on-line using a Patient Data Portal 117, which is controlled by a Patient Data eHistory & Physical subprogram and specialized a graphical user interface (GUI). The patient information regarding the results of initial consults, clinical history reviews, and physicals are input into the data processor and storage system using the eHistory & Physical subprogram. Likewise, the progress of the patient can be monitored and updated by the hospitalist using an eProgress Note subprogram shown in the Home Screen 101 of FIG. 1. The information in the Patient Data Portal, Patient Data eHistory & Physical subprogram, and eProgress Note subprogram may be accessed from, or input into, the data processor and storage system using a desktop data processor and storage device, mobile phone, intelligent pad devices, or other personal communication device.

The eProgress Note subprogram will provide User feedback while a graphical user interface is completed with the patient progress information, with the feedback giving the doctor, physician, hospitalist or User other queries for information, suggestions on how to complete answers, suggested responses or lists of responses, or other relevant information. Other graphical user interface forms used in other subprograms can also provide the same type of User feedback when the User is providing responsive information to the system subprogram, such as the other queries for information, suggestions on how to complete answers, suggested responses or lists of responses, or other relevant information.

The User can also access the Statistics subprogram Dashboards, Survey Results and Revenue Reports screens shown in FIGS. 16 and 17 from the Home Screen 101 through the SSRS subprogram screen 103 shown in FIG. 1. The User can also input, modify and access patient information or physician information from the patient and physician subprograms pages, respectively. When the User is permitted to access information for a particular patient, the User can gage patient progress, physical information, treatment administered, or other patient information relating to test results, medication, eProgress Notes, and diagnosis.

The doctor, hospitalist or User can also access Statistics information that will allow him or her to gage their respective workloads compared to other doctors, hospitalists, or Users. The identity of other doctors, hospitalists, or Users may or may not be concealed or hidden from general access to all Users, but the doctor, hospitalist, or User can gage his workload against his co-workers to determine whether he or she is within standards for workload, behind or ahead of co-workers in terms of workload completed, or slower or faster than co-workers in terms of workload completion. The dashboards on FIG. 16 show bar charts, speedometer settings, line charts, and numerical tables so the User can judge his or her performance against a broader metric. By providing this comparative metric information to the User (e.g. comparing performance versus group of other users or other hospitalists), increases in worker productivity are possible, as well as highlighting areas where patient care can be enhanced through the identification of User or physicians that may not be expending sufficient time on particular cases or patients. In addition to gauging relative productivity, the User can also examine his or her individual performances to estimate the fees and wages that may be due to him or her for their work at the facility or with the patient.

All the physician or user information relating to a particular patient can be reviewed with the other physicians or users working with or treating the patient being identified to the User accessing the data processor and storage control system, as well as the pertinent information regarding patient progress, physical information, treatment administered, or other patient information relating to test results, medication, eProgress Notes, and diagnosis. The information relating to the Statistics, patient and physician subprograms may be accessed from, or input into, the data processor and storage system using a desktop data processor and storage device, mobile phone, intelligent pad devices, or other personal communication device.

Pre-defined specifications are shared with facility and then the software program controls the additional method that takes into account the differences of the hospital data, normalizes to HNI specifications, and populates the appropriate tables and fields in the storage. This action occurs either "on demand" or with a scheduler. The workflow process begins as the census is applied to the application. The invention also includes a method to manage workflow for discharged patients. The present invention assimilates demographic, diagnosis code, charge codes, administrative, financial, and clinical data. This embodiment comprises a web-based, active server page (ASP) that provides real-time demographic, financial and clinical information. A user may access the system through any standard web browser operated on a computing device connected to the Internet or other network.

The system shown in FIG. 2 supports continuity of care through enhanced communication and notification with relevant clinical and operational providers, and the ability to manage patient and treatment files and patient medical information using specialized subprograms and indexing and referential storage improves the efficiency and performance of hospital information systems by improving and integrating communications. Moreover, the system and method of the present invention allows a hospital facility to take appropriate actions regarding the projected resource intensity required for the appropriate care of patients in the hospital facility.

The present invention as shown in FIG. 2 is a specialized system and method, which includes specialized data processor and storage readable medium and subprograms that are not available in a generic computer device, even though a user/provider accesses the system through a standard web browser on a computing device or connection to the Internet or single or multi-tier network. The method provides a graphical user interface (GUI) by a content server, which is hardware or a combination of both hardware and software. A user, such as a health care provider, can be given remote access through the GUI to view or update information about a patient's medical condition using the user's own local device (e.g., a personal data processor and storage or wireless handheld device). When a user wants to update the records, the user can input the update in any format used by the user's local device.

The ability to manage patient diagnosis and treatment files and information will improve physician communication and integration into hospital information systems. The system and method of the present invention allows a hospital facility to take appropriate actions regarding the projected resource intensity required for the appropriate care of patients in the hospital facility. This system supports continuity of care through enhanced communication and notification with relevant clinical and operational providers.

The interactions of the specialized protocols in FIG. 2 begin at Start 201 that goes to the Provider Login 205. The Provider Login 205 proceeds to the HNI Credentials Validation 210 at step 207, which then proceeds to the Facility protocol 215 at step 209. The Facility protocol 215 can proceed to the Data Capture protocols 285 at step 208, which is coupled by connection 219 to the Hospital Data storage 277 located in the HNI Connect DataStore 275.

The Facility protocol 215 can also proceed to the Charge Capture-Quick Entry protocols 220 by step 211, which will proceed to the EM Code-Level protocol 250 by step 217, which will then proceed to the Diagnosis DX step 280 by step 218, which will then proceed to Additional Procedures protocols 290 by step 221. The Charge Capture-Quick Entry protocols 220 can proceed to the Census protocols 230 by step 213, which will then proceed to the Provider/User Census protocols 260 by step 224, which will then proceed to the Group Census 295 by step 223, which will then proceed to the Bi-Directional Transfer protocols 293 by step 222.

The Census protocols 230 can proceed to the Medical Director Reports protocols 240 by step 214, which is coupled by connection 228 to the Physician Data storage 292 located in the HNI Connect DataStore 275. The Medical Director Reports protocols 230 can also proceed to the Administration/Medical Officer protocols 270 by step 226, which is coupled by connection 227 to the HNI Connect Knowledge Data storage 283 located in the HNI Connect DataStore 275. The Physician Data storage 292 is coupled to the HNI Connect Knowledge Data storage 283 by connection 229, and the HNI Connect Knowledge Data storage 283 is connected to the Hospital Data storage 277 by connection 231.

The Census protocols 230 allow the User to access Provider/User Census 260 information, Group Census 295 information, or Bi-directional Transfer 293 information. Further, the data processor and storage control software supports the admission and discharge of patients using the Quick Entry protocols 220, including the ability to transfer patients to other facilities and the care of other physicians. When a User wishes to transfer a patient's care to another physician, the Bi-Directional Transfer 293 protocols or the Quick Entry 220 protocols may be used. After User Login, the User chooses the patient being transferred and puts in a description of why the transfer is occurring, the status of the patient, the identification of the new physician, hospitalist, or facility where the patient is being transferred to. The information relating to the patient transfer may be accessed from, or input into, the data processor and storage system using a desktop data processor and storage device, mobile phone, intelligent pad devices, or other personal communication device, and the physician, hospitalist, or User to whom the patient is being transferred will receive an email, text message or other notification about the transfer of patient care. That doctor, physician or hospitalist will be added to the Users having rights and privileges to that particular patient's information.

The storage 292, 283 and 277 in the HNI Connect Datastore 275 are coupled to the HNI Operations protocols 294, which include the Physicians protocols 291 connected by connection 299 to the HNI Analytics protocols 296, which is connected by connection 298 to the Administrative Reports protocols 297. The patented invention stores data in a more efficient and effective manner than previously used in other data storage systems through the use of an enhanced performance data storage sub-system using a self-referential, indexed data storage protocol and procedure that store all entity types in a single table after indexing is performed to prevent the creation of duplicative data entries in the data storage sub-system. The indexing protocols and procedures used in the enhanced data storage sub-system of the present invention reviews input data (received in health level 7 or HL7 format), and, before the creation of a new record in the data storage sub-system, the enhanced data storage sub-system of present invention using a self-referential, indexed data storage protocol and procedure searches existing records in the data storage sub-system to determine if the patient whose data is being reviewed was previously admitted into a particular hospital facility, a surrounding hospital facility, or any other related hospital facility connected to the present invention system.

If the enhanced data storage sub-system of present invention using a self-referential, indexed data storage protocol and procedure determines that the patient's data being reviewed relates to a patient that was previously admitted into a particular hospital facility, a surrounding hospital facility, or any other related hospital facility connected to the present invention system, then no new record for the patient is created in the data storage system and the input data is directed to the previously created record for that patient. If the enhanced data storage sub-system of the present invention using a self-referential, indexed data storage protocol and procedure determines that the patient's data being reviewed does not relate to a patient that was previously admitted into a particular hospital facility, a surrounding hospital facility, or any other related hospital facility connected to the present invention system, then a new record for the patient is created in the data storage system and the input data is directed to this new record for that patient.

A new record for a patient is only created when it is necessary, and when that patient has not been previously admitted into a particular hospital facility, a surrounding hospital facility, or any other related hospital facility connected to the present invention system. If the new data received for a patient relates to a patient that was previously admitted into a particular hospital facility, a surrounding hospital facility, or any other related hospital facility connected to the present invention system, no new patient record is created and the input data is directed to the previously created records in the data storage system. The avoidance and elimination of duplicate records creation for patients that were previously admitted into a particular hospital facility, a surrounding hospital facility, or any other related hospital facility connected to the present invention system results in a greater efficiency and effectiveness in the storage of patient records than has been previously known in the prior art data storage systems.

The present invention's use of an enhanced performance data storage sub-system using a self-referential, indexed data storage protocol and procedure supports record storage in a table after indexing, which also allows for faster searching of data stored therein compared to other data storage systems. Moreover, the enhanced performance data storage sub-system using a self-referential, indexed data storage protocol and procedure in the present invention allows for more effective storage of data than other data storage systems, such as image and unstructured data storage. And, the enhanced performance data storage sub-system using a self-referential, indexed data storage protocol and procedure in the present invention provides for more flexibility in the configuration of the data and records stored therein over other data storage systems.

Once a provider has logged into the information system and been validated for the system, an individual patient may be selected from the provider's census listing, and from the patient's data field, the Quality Panel screen can be accessed. The Quality Panel displays information related to measures that assess the cost of care, resources used to provide care, inappropriate use of resources, or efficiency of care delivered. Patient information on the Quality Panel is populated from the patient data input into the primary storage of the Hospital Information System.

One of the crucial data points input for a hospitalized patient is allocation of an accurate diagnosis. Treatment for a hospitalized patient is diagnosis-specific as is the allocation of resources required for treating that patient. In medical records, especially in Electronic Medical Records (EMR), diagnoses are assigned unique codes called Diagnosis Related Grouping codes or DRGs. Working DRGs are defined by Diagnosis Related Groups (DRGs) allocated on admission based on the patient's presenting problem or provisional diagnosis. For DRGs, patients are categorized with respect to diagnosis, treatment, and predicted length of hospital stay (GMLOS). DRGs are assigned based on a number of variables, including: principal diagnosis; secondary diagnosis(es); surgical procedures performed; co-morbidities and complications that may affect treatment (such as diabetes or pulmonary disease); age and sex of the patient; and discharge status. Patients and DRGs are then concurrently reviewed until discharge. Actual Length of Stay (LOS) for patients can be compared to the GMLOS predicted by the working DRG.

The present system and method provide for identification, documentation, analysis and display of essential data for working DRGs, including providing multiple options for entry of diagnosis data; and providing a comprehensive analysis of diagnosis codes entered for a specific patient for related assessment points, such as length of stay (LOS), geometric mean length of stay (GMLOS), variance between LOS/GMLOS; DRG weight, risk adjusted factors (RAF), severity of illness (SOI) and risk of mortality (ROM), and providing an alert for a missing diagnosis. Additionally, the system automatically identifies and highlights risk adjusted diagnosis codes that may affect the above analysis, such as Complication or Comorbidity codes (CC) and Major Complication or Comorbidity codes (MCC).

The original intent of DRGs was to identify the "products" provided by a hospital, such as a procedure like an appendectomy. Since patients within each category or group are assumed to be clinically similar and are expected to use the same level of hospital resources, DRG payments are based on the care given to and resources used by a "typical" patient within the group. DRGs have been used in the U.S. since 1982 to determine how much Medicare pays hospitals for each such "product" it provides. While DRGs were originally used to determine standardized payments under Medicare, similar prospective payment systems are now also utilized by many private insurers.

The majority of patients admitted to hospitals have some form of medical coverage, either private medical insurance, or Medicare/Medicaid. Hospitals are reimbursed for medical care directly by the insurer. The present foundation for determining reimbursement to health care facilities is primarily through diagnosis-related groupings (DRGs). When a patient is admitted to a hospital, the reason for the admission is categorized by one or more diagnosis codes and DRG codes for those diagnoses are assigned based on standardized diagnosis codes in conjunction with demographic information and coexisting conditions. These DRGs are based on the principal that patients with similar diagnoses would likely spend about the same amount of time as an inpatient and require similar resources while hospitalized. DRGs are how Medicare, Medicaid, and many other health insurance companies categorize hospitalization costs and determine how much to pay for a patient's hospital stay. Rather than paying the hospital for what was actually spent caring for a hospitalized patient, Medicare pays the hospital a fixed amount based on the patient's DRG code. The DRG classification system standardizes prospective payment to hospitals and encourages cost containment initiatives. A DRG payment is generally expected to cover all charges associated with an inpatient stay from patient admission to until discharge. The DRG also includes any services provided by outside providers. For these reasons, it is essential to identify and record accurate diagnosis codes, as well as any complications or comorbidities that exist for the patient to ensure accurate DRG codes for reimbursement and accurate medical records.

Complications are conditions that arise during a hospital stay that prolong the length of stay. Infection and hemorrhage are examples of complications that may occur following a surgical procedure that would prolong a patient's length of stay. Diagnoses are updated or added when complication occur. Comorbidities are preexisting conditions, such as diabetes, heart disease or pulmonary disease, which may affect the treatment received and/or prolong a patient's length stay, and comorbidities, if known, are included in the initial entry of the diagnoses entered for a patient. For example, a patient who presents with a fractured ankle, and who also has diabetes, will likely require additional resources and a longer hospital stay, than a patient of similar age and injury who does not have diabetes.

Hospitals and other health-care facilities will be reimbursed by Medicare or other insurers for a set amount associated with the DRG codes for a patient's treatment. If a hospital treats a patient while spending less than the prospective DRG payment, it makes a profit. However, if a hospital spends more than the prospective DRG payment treating a patient, it has a loss. Assigning accurate diagnosis codes, which encompass any secondary diagnoses, complications or comorbidities, is therefore essential for all hospitals and healthcare facilities, not only for the purpose of receiving appropriate reimbursement for services rendered, but also, in order to accommodate new patients, allocate resources, including personnel, and deliver healthcare effectively and efficiently. A system and method is needed to accurately record, analyze and report Working Diagnosis Related Groups, identify accurate diagnoses and analyze diagnosis codes to determine relevant diagnosis data, in order to improve patient care, increase overall hospital efficiency and decrease revenue.

DRGs are assigned based on ICD (International Classification of Diseases) diagnoses, procedures, age, sex, discharge status, and the presence of complications or comorbidities. The ICD is the international standard diagnostic tool used for epidemiology, health management, and clinical purposes, and is used to assist in the storage and retrieval of diagnostic information. The ICD system is used by physicians and other healthcare providers to classify and code all diagnoses, symptoms, and procedures recorded in conjunction with hospital care. The ICD is maintained by the World Health Organization (WHO) and was designed as a health care classification system to provide a system of diagnostic codes for classifying diseases, including nuanced classifications of a wide variety of signs, symptoms, abnormal findings, complaints, social circumstances, and external causes of injury or disease. This system is designed to map health conditions to corresponding generic categories together with specific variations, assigning for these a designated code, up to six characters long. The ICD system is used by physicians and other healthcare providers to classify and code all diagnoses, symptoms and procedures recorded in conjunction with hospital care.

Working DRGs are defined by Diagnosis Related Groups (DRGs) allocated on admission based on the presenting problem or provisional diagnosis. Patients and diagnosis codes are then concurrently reviewed until discharge. Actual Length of Stay (LOS) of patients can be compared to the GMLOS predicted by the working DRG. Diagnosis codes for a patient are available in real-time following entry into the system. Factoring the working DRG begins with the submission of one or more Dx (diagnoses) codes. After accessing patient census information, the User, usually a physician, clicks on a patient's name resulting in a more detailed view of the patient's record on the Quality Panel screen 300 and revealing the Quality Panel 310, as seen in FIG. 3A.

Figure 3A:
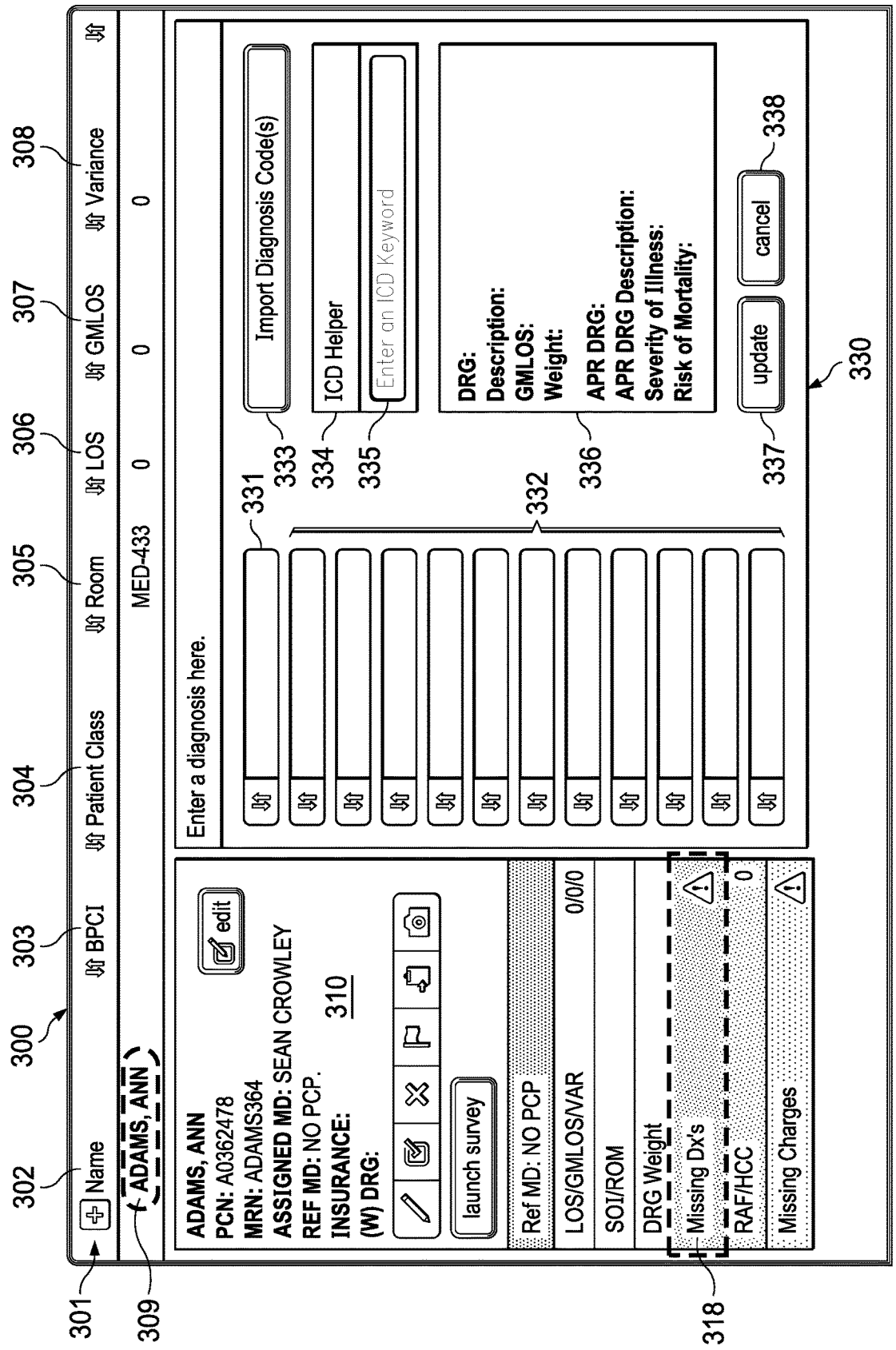
FIG. 3A shows a view of a Quality Panel screen for a selected patient.

The Quality Panel screen 300 seen in FIG. 3A has a patient census bar 301 with headings for, optionally, patient name 302, BPCI (Bundled Payments for Care Improvements) 303, Patient Class (e.g., Inpatient, Outpatient, ER,) 304, Room number 305, LOS (Length of Stay) 306, GMLOS (Geometric Mean Length of Stay) 307, and Variance (difference between LOS and GMLOS) 308.

Figure 3B:
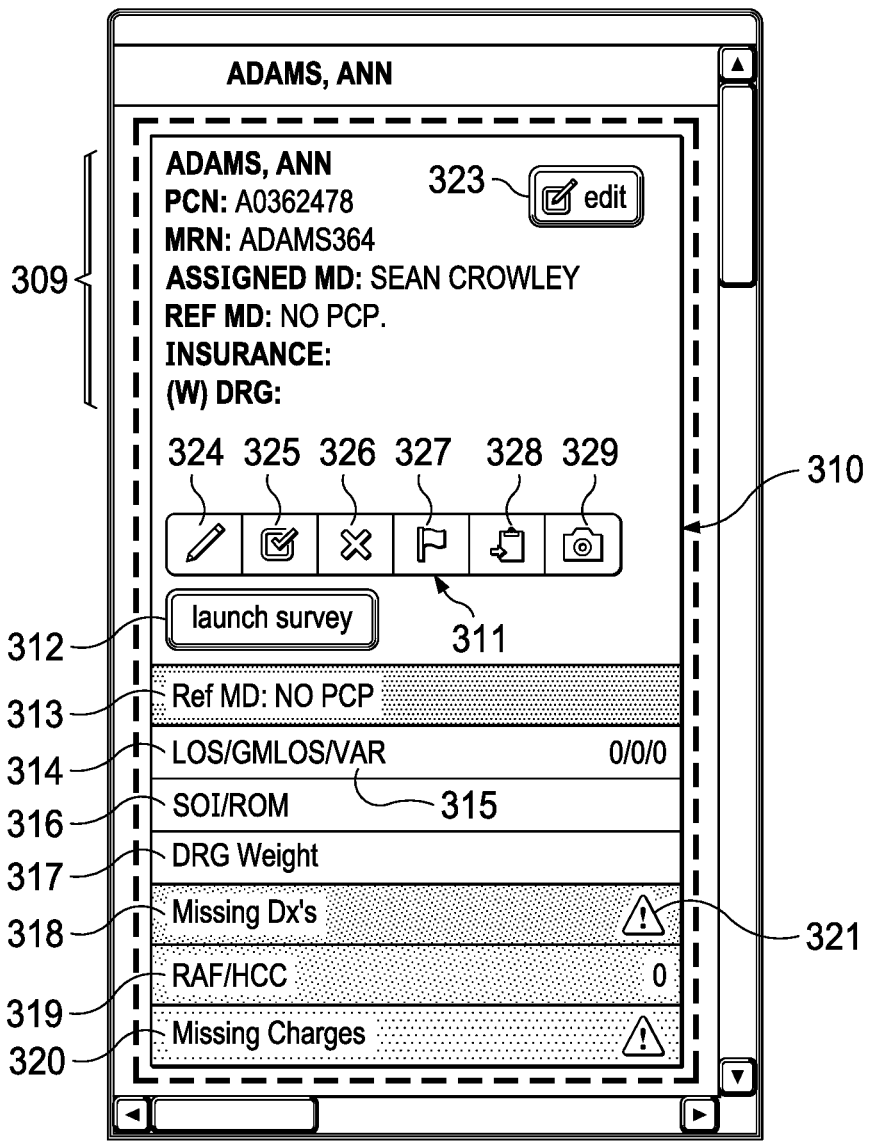
FIG. 3B shows a detail of the Quality Panel seen in FIG. 3A.

As seen in the FIG. 3B enlargement, the patient data display 309 shows details for the selected patient for each of the above header bar options. The Quality Panel screen 300 displays a patient's current data in the Quality Panel 310, including, patient name, PCN (Primary Care Network), MRN (Medical Records Number), Assigned MD, Referring MD, Insurance, and (W) DRG (working diagnosis related group).

A number of action buttons are provided on the Quality Panel to allow for management of data. A launch survey action button 312 sends a customized survey for the selected patient to complete prior to discharge and an Edit action button 323 allows for editing of the Quality Panel data. A series of action buttons 311 allows the physician to add, manage or transfer data associated with the case. The pencil action button 324 functions to add physician notes on the case. The check-mark action button 325 allows the physician to electronically "check-out" of a case at the end of a shift. The X-mark action button 326 deletes that case from the physician's case listing. The flag action button 327 opens a data entry screen to report discharge delays that result in avoidable days. The clipboard action button 328 allows for a copy of the patient information to be sent electronically when a patient is transferred to another facility, such as a skilled nursing facility. The camera action button 329 takes a snapshot of the screen image that may be used for identification of a case. For example, the snapshot can be used in face-sheets associated with the case to give the physician an at-a-glance summary of the case.

The Quality Panel 300 has navigation bars that will display additional data in an adjacent window when actuated. Navigation bars include: Referring physician (Ref MD) 313, LOS/GMLOS/Variance (length of stay ratio) 314, SOI/ROM (Severity of Illness/Risk of Mortality) 316, DRG weight 317, Edit DX (edit diagnosis) 318, RAF/HCC (Risk Factor Adjustment/Hierarchal Condition Category) 319, and Missing Charges 320. Each navigation bar also displays the current data for that item. Variance 315 can also be displayed on a navigation bar separate from LOS/GMLOS and will display the variance shown in the patient census bar.

LOS/GMLOS/Variance: LOS/GMLOS/variance 314 is a comparison of actual LOS to the projected LOS and variance is the difference between the two. Variance numbers change over the inpatient days with a positive number indicating that actual LOS is greater than projected and a negative number indicating the actual LOS is less than projected. Optionally, Variance for the LOS/GMLOS can be shown on a separate navigation bar from the LOS/GMLOS.

SOI/ROM: Severity of Illness/Risk of Mortality (SOI/ROM) 316 is a measure of the overall severity of the illness. Severity of illness is defined as the extent of organ system derangement or physiologic decompensation for a patient. Patients with higher SOI (e.g. major or extreme) are more likely to consume greater healthcare resources and stay hospitalized longer than patients with lower SOI in the same DRG. Severity is rated as Minor (1), Moderate (2), Major (3), and Extreme (4). Risk of mortality (ROM) provides a medical classification to estimate the likelihood of in-hospital death for a patient. The ROM class is used for the evaluation of patient mortality. The ROM classes are Minor (1), Moderate (2), Major (3), and Extreme (4).

DRG Weight: Each diagnosis code has a DRG weight 317 associated with it that estimates the average level of resources required to treat a patient with that diagnosis. The higher the number, the greater the level of estimated resources for treating a patient, with the estimate taking into consideration both the labor and non-labor resources that will be required. Reimbursement to a healthcare facility for a patient's care is based on the facility's base payment rate and the DRG weight associated with the patient's diagnosis.

RAF/HCC: The Risk Factor Adjustment (RAF) 319 is a relative measure of the probable costs to meet the healthcare needs of an individual Medicare beneficiary. Hierarchical Condition Category (HCC) is a resource for predictive cost expenditures for an individual based on demographic information and health status information. Medicare assigns a Risk Adjustment Factor or RAF score, to each eligible beneficiary based on health conditions the beneficiary may have, specifically, those that fall within a Hierarchical Condition Category (HCC), as well as demographic factors such as Medicaid status, gender, aged/disabled status, and whether a beneficiary lives in the community or in an institution.

Missing Charges: Missing Charges 320 is an indicator to alert a provider that charge codes have not been entered for one or more hospital days. If charges are missing, an alert icon will inform the provider that charges are missing and actuating the bar will allow the provider to enter the necessary data. A Missing Charges may show on the navigation bar during the entry process for a new patient until a charge code is provided.

Diagnosis Entry: As seen in FIGS. 3A and 3B, on the Diagnosis navigation bar 318, an alert icon 321 is shown which indicates a diagnosis is missing for the selected patient. The absence of any diagnosis (Dx) codes is easily identifiable to the provider by the "Missing Dx's" text in the navigation bar 318 and by a red background in the navigation bar. In FIG. 3A, the diagnosis navigation bar 318 has been actuated, and has opened the diagnosis entry screen 330 showing options for entering one or more diagnoses. If a diagnosis has been previously entered, the navigation bar will display "Edit Diagnosis," and actuating the navigation bar 318 will open the diagnosis entry screen 330 and allow the User to modify the diagnosis.

Although a minimum of one diagnosis code is required, including the full bundle of appropriate diagnosis codes is recommended at the outset, beginning with the primary diagnosis code. A patients may present with a straightforward uncomplicated diagnosis, such as a broken leg, influenza or other single condition, which can be adequately described with a single diagnosis code. Often, however, a patient will have one or more underlying conditions, such as heart disease, asthma, or other comorbid condition, which will affect treatment options and the resources required for treatment, as well as any associated length of stay for that patient. For example, a patient presenting with influenza, who also has heart disease and asthma, will most likely require more time and resources to treat. It is, therefore, important for the provider to enter the appropriate codes that take these comorbid conditions into account when entering the diagnosis into the system.

There are multiple options for entering diagnosis codes at the diagnosis entry screen 330 which will be described herein. The diagnosis can be manually entered directly into the primary diagnosis field 331 or one of the secondary diagnosis entry fields 332, or a diagnosis can be selected from a dropdown menu generated by entry of two or more characters into the diagnosis field. A diagnosis can be imported from a patient's existing electronic medical record (EMR) by actuating the import diagnosis navigation bar 333, or an ICD diagnosis code can be manually entered directly into the ICD entry field 335 or and ICD code can be selected from a list auto-generated by entering data in the field. When entering diagnosis codes, providers can use the ICD number identifier, the ICD description, commonly used abbreviations or customizable abbreviations to enter data or search for diagnosis options.

When a diagnosis has been entered, the diagnosis and associated ICD code will show in the primary diagnosis field 331 and additional diagnoses added will show in one or more of the subsequent diagnoses fields 332. When a diagnosis has been entered, the diagnosis quality panel 336 will auto-populate with the data associated with the diagnosis. In FIG. 3A, no diagnosis has been entered yet, therefore no data is displayed in the diagnosis quality panel 336. The update button 337 is used to accept the entry into the system and the cancel button 338 will cancel the entry.

ICD Code Entry: If the ICD diagnosis code is known, the number can be entered directly into the ICD entry field 335 on the diagnosis entry screen 330, and the corresponding descriptive diagnosis text will be visible in the primary diagnosis field 331 or one of the secondary diagnosis fields 332. If part of a code is entered, the ICD Helper 334, will suggest matching codes which may be selected. Once a diagnosis code is entered, the diagnosis quality panel 336 will auto-populate with the data calculated for the specific diagnosis.

Figure 4B:
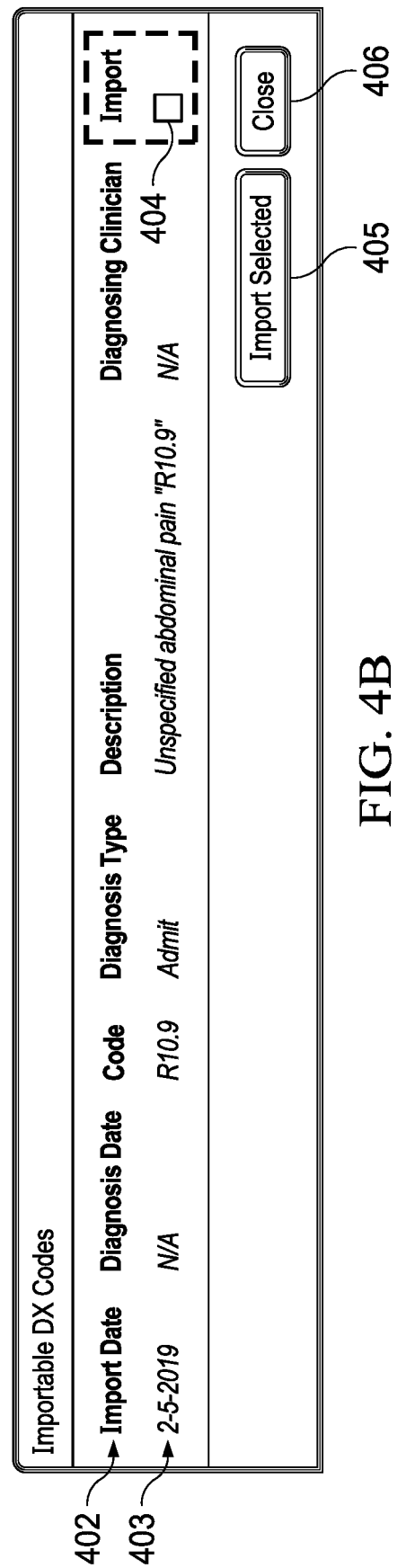
FIG. 4B shows an importable diagnosis codes screen.

Import Diagnosis Codes: When the system is connected to a facility's EMR, the provider has the option of importing any available diagnosis codes from the EMR by clicking on Import Diagnosis Code(s) navigation bar 401, as seen in FIG. 4A. Actuating the Import Diagnosis Code bar will access any EMR records available for the selected patient. If EMR records are available for the patient, an import screen, as seen in FIG. 4B, will appear. Data descriptions listed in the header bar 402 of the import screen include: import date, diagnosis date, code, diagnosis type and description, and a data field 403 for the selected patient's previous admission are shown. A data field can be selected for import by clicking the import button 404. When the desired one or more data rows have been selected, actuating the import selected button 405 will import the selected diagnosis codes and diagnosis descriptive text into the diagnosis entry screen in one or more of the diagnosis fields (331, 332). Clicking the close button 406 will close the import screen and return the user to the diagnosis entry screen. Once a diagnosis code is imported, the diagnosis quality panel 336 will auto-populate with the data calculated for the specific diagnosis.

Enter Diagnosis Description: A diagnosis can also be entered by providing descriptive terms. As seen in FIG. 5, entering at least two letters in the primary diagnosis field 501, will generate a dropdown menu 502 of matching suggestions. As seen in the dropdown menu 502, entry of "ch" in the primary diagnosis field generated diagnosis options that begin with the selected letters, such as "chest pain," and diagnosis options that contain the selected letters, such as "tachycardia." The selectable choices in the dropdown menu 502 will narrow down as additional characters are entered in the diagnosis entry field. Clicking on the selection in the dropdown menu will enter the diagnosis descriptive text and the associated ICD code into the primary diagnosis entry field 331. Additional diagnoses can be entered by repeating the process in one or more of the secondary diagnosis entry fields 332. Once a diagnosis is selected, the diagnosis quality panel 336 will auto-populate with the data calculated for the specific diagnosis.

Diagnosis Identifiers: When selecting a diagnosis code, the User can easily ascertain additional details of a particular diagnosis code based on unique identifiers contained in the text description and visual presentation of the diagnosis code. Diagnosis codes can be considered as Risk Adjusted Codes, Major Complication or Comorbidity (MCC) codes; Complication or Comorbidity (CC) codes; or Standard ICD codes with no known complication or comorbidity. Each diagnosis code has a DRG weight associated with it that estimates the average level of resources required to treat a patient with that diagnosis. When a diagnosis also includes risk adjusted codes, MCC codes and CC codes, the patient's overall diagnosis is affected and this will often result in a substantial effect on the on the projected length of stay and DRG weight calculated for a patient based on the diagnosis.

Figure 6A:
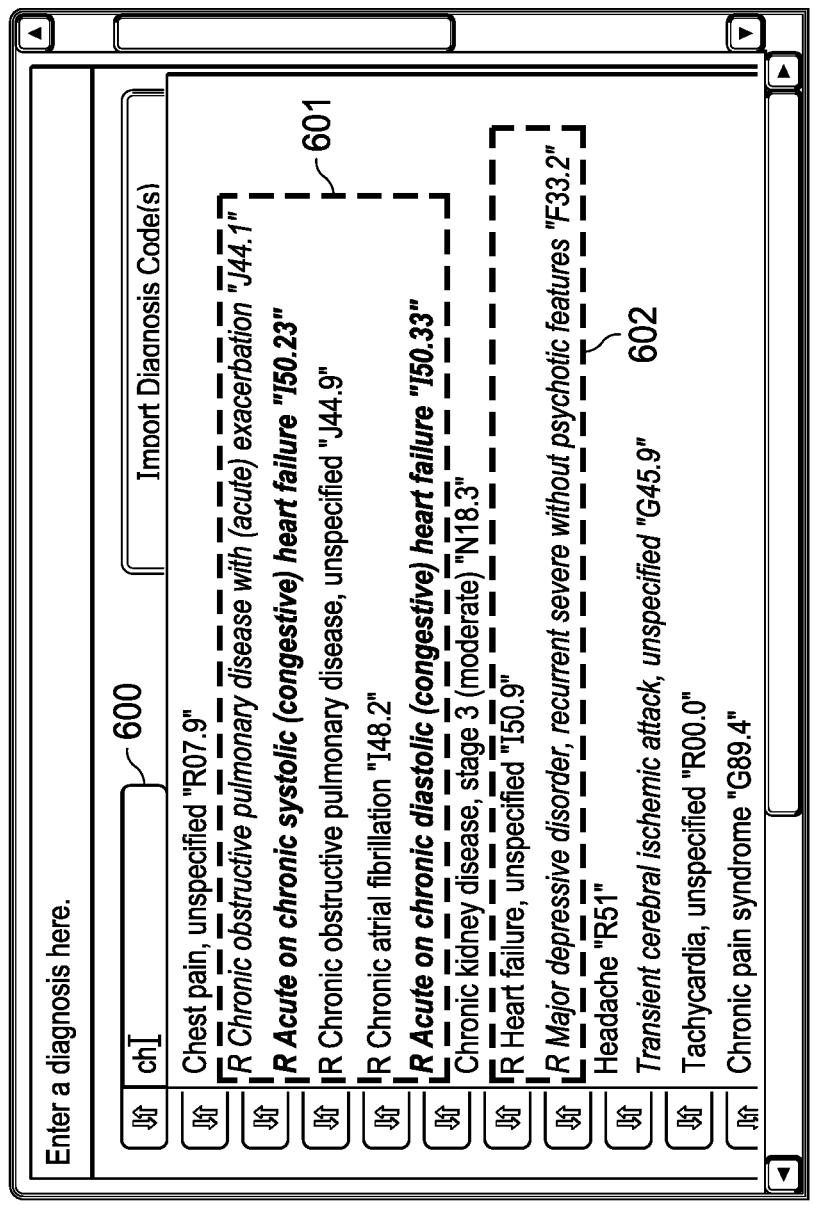
FIG. 6A shows a dropdown menu with Risk Adjusted Dx Codes.

Risk Adjusted Codes: As seen in FIG. 6A, Risk Adjusted codes begin with a capital "R" in the matching diagnosis suggestion list. In the primary diagnosis entry field 600, the entered characters "ch" have generated a dropdown menu with multiple possible diagnoses, and several of the diagnosis codes start with an "R" (boxes 601 & 602) indicating these are risk adjusted codes, such as the entry for "R Acute on chronic systolic (congestive) heart failure I50.23."

Figure 6B:
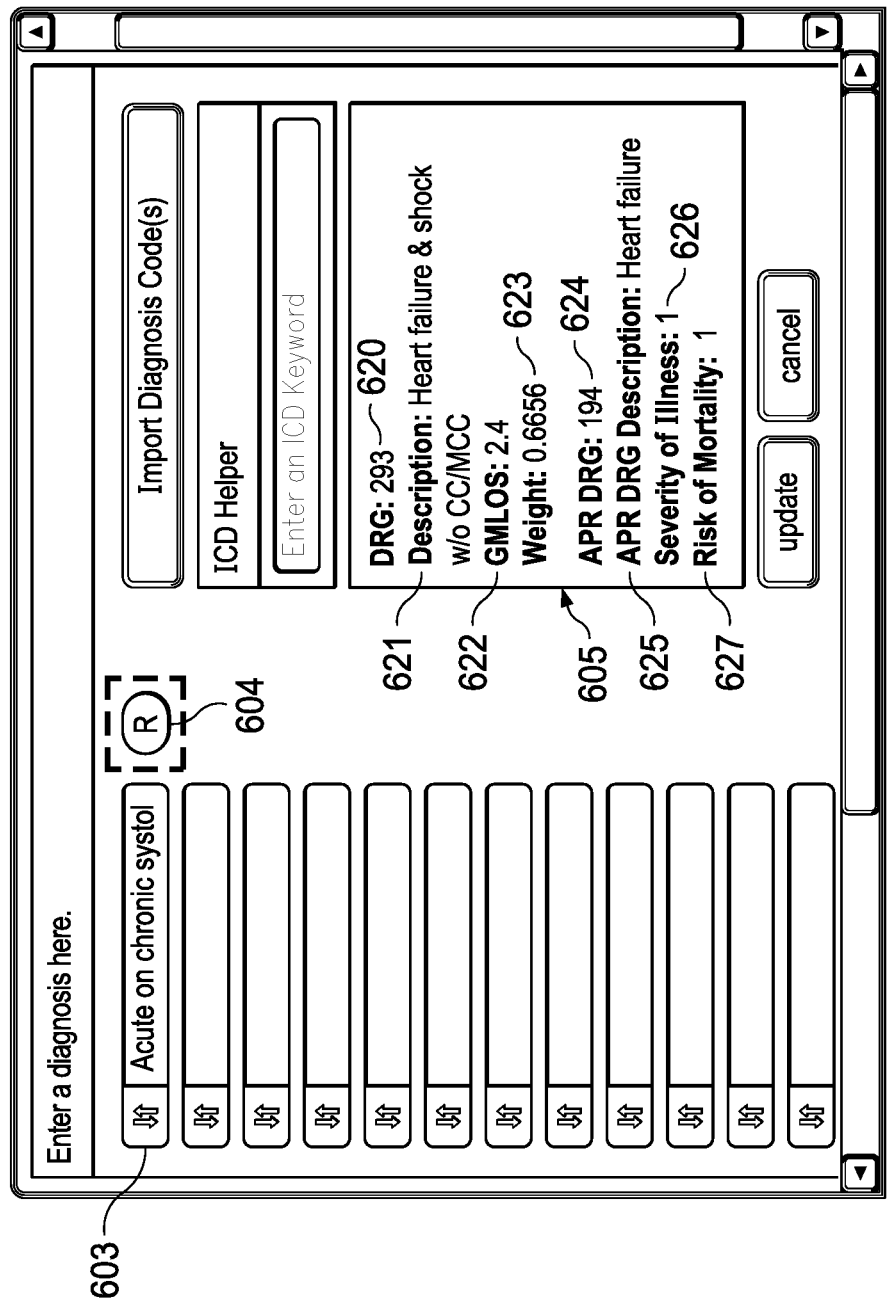
FIG. 6B shows Risk Adjusted Codes marked with an "R" in the diagnosis field.

As seen in FIG. 6B, once a diagnosis has been selected and saved, the diagnosis description and ICD code appear in the diagnosis field 603 and an "R" symbol 604 is visible next to the diagnosis field indicating that the entered diagnosis code is a risk adjusted code. When the diagnosis has been selected and saved, the diagnosis data is auto-populated into the diagnosis quality panel 605. DRG details and APR DRG (All Patients Refined Diagnosis Related Grouping) details are included data for the diagnosis quality panel 605. While DRGs are used by Medicare to measure the typical resource use of an inpatient stay, APR DRGs, in addition to resource utilization, also include a more detailed DRG breakdown for non-Medicare patients, including measures of severity of illness and risk of mortality, with patient age considered in the severity leveling.

In the example in FIG. 6B, the entered diagnosis is "R Acute on chronic systolic (congestive) heart failure I50.23" and the diagnosis quality panel 605 now displays details specific to that diagnosis, including: DRG: 293 (620); Description: Heart failure & shock w/o CC/MCC (621); GMLOS: 2.4 (621); Weight: 0.6656 (623); APR DRG: 194 (624); APR DRG Description: Heart failure (625); and Severity of Illness: 1 (626); and Risk of Mortality: 1 (627).

Figure 6C:
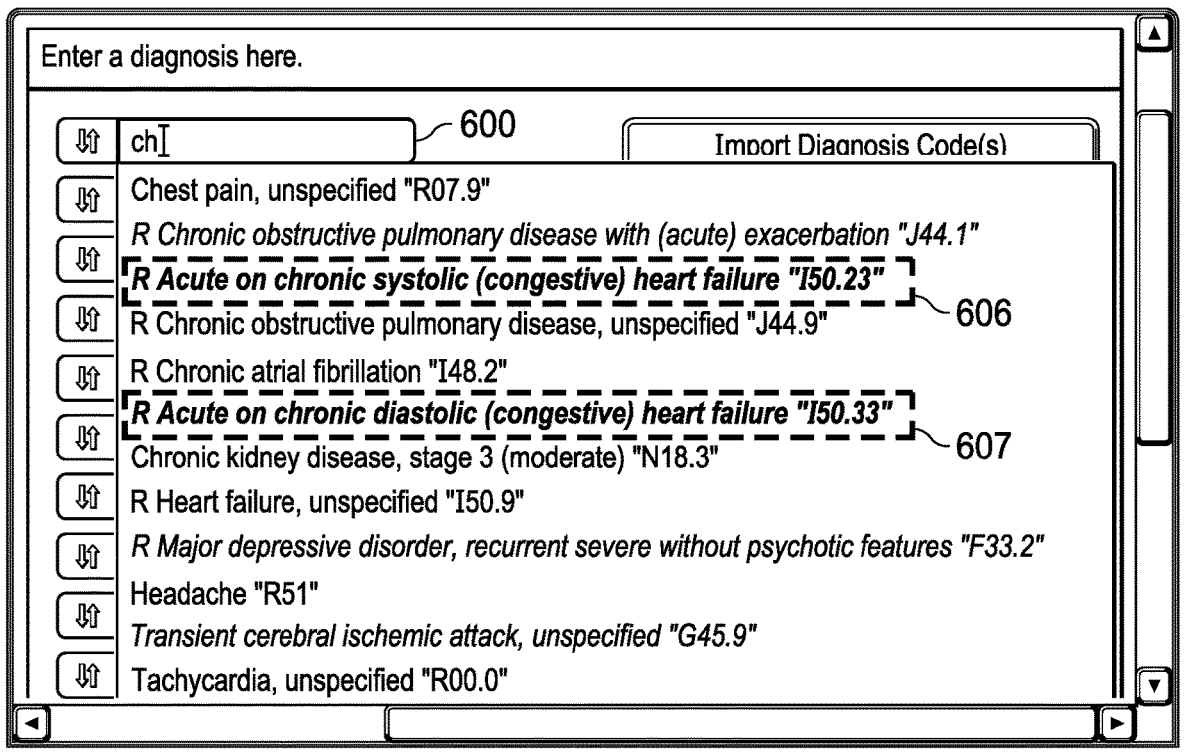
FIG. 6C shows a presentation of Major Complication or Comorbidity (MCC) codes.

Major Complication or Comorbidity (MCC) codes: Major Complication or Comorbidity are secondary diagnoses that will likely have a profound effect on the resource intensity required to treat a patient when taken into consideration with the primary diagnosis. In FIG. 6C, of the diagnosis choices generated in the dropdown menu from the entry of 'ch" in the primary diagnosis entry field 600, two of the choices (606, 607) are considered to be major complications or comorbidities. Most of the major complications or comorbidities diagnoses will also be indicated as risk adjusted and begin with "R." When viewed in the on-screen dropdown menu, the major complications or comorbidities diagnoses are presented in red bold text. For the purpose of illustration, here these diagnoses are presented in bold text.

Figure 6D:
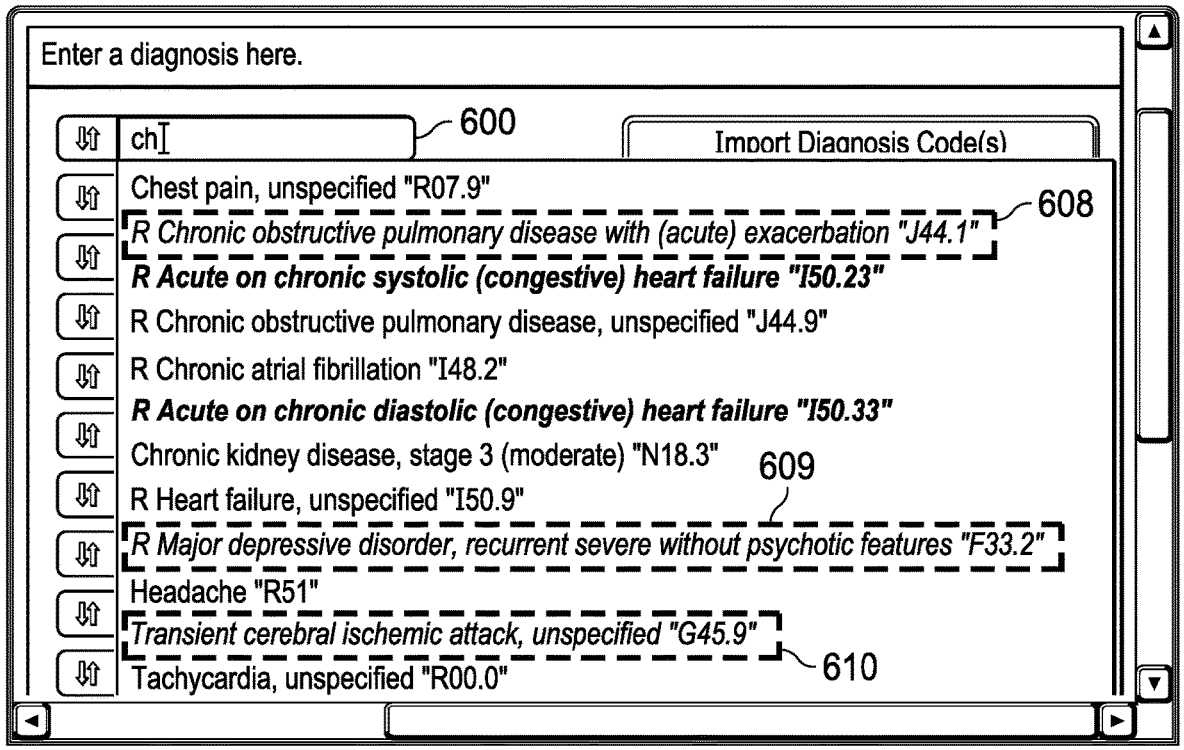
FIG. 6D shows a presentation of Complication or Comorbidity (CC) codes.

Complication or Comorbidity (CC) codes: Complication or Comorbidity are secondary diagnoses that will potentially have an effect on the resource intensity required to treat a patient when taken in consideration with the primary diagnosis, but are generally less severe than a secondary MCC. In FIG. 6D, of the diagnosis choices generated in the dropdown menu from the entry of 'ch" in the primary diagnosis entry field 600, three of the choices (608, 609, 610) are considered to be complications or comorbidities. Some of the complications or comorbidities diagnoses will also be indicated as risk adjusted and begin with "R". When viewed in the on-screen dropdown menu, these diagnoses are presented in orange bold text. For the purpose of illustration, here these diagnoses are presented in italic text.

Standard ICD codes with no CC or MCC: Standard ICD codes are diagnoses that do not have associated complications or comorbidities. A few of these diagnoses will also be indicated as risk adjusted and begin with "R." In FIG. 6E, of the diagnosis choices generated in the dropdown menu from the entry of 'ch" in the primary diagnosis entry field 600, several of the choices (611, 612, 613) do not have associated complications or comorbidities. When viewed in the on-screen dropdown menu, these diagnoses are presented in black, non-bold text. For the purpose of illustration, here these diagnoses are presented in standard black text without bolding or italicizing.

Diagnosis Overview: The MCC, CC and risk adjusted diagnoses are presented in colored or bold text, or with a leading "R," allowing the provider to easily ascertain details of a particular code based on these unique identifiers and allowing the provider to determine which of the codes are likely to affect the DRG weight for a specific diagnosis.

Inclusion of a secondary diagnosis can affect the DRG weights and these changes will be reflected in the data presented in the diagnosis quality panel. As seen in the example in FIG. 7, the primary diagnosis field 701 has a diagnosis of "R Acute on chronic systolic (congestive) heart failure I50.23." This diagnosis is a Risk Adjusted diagnosis as indicated by an "R" next the associated diagnosis field 702. A secondary diagnosis of "Cardiac arrhythmia, unspecified" has been entered in the secondary diagnosis field 703 and the details in the diagnosis quality panel 704 are the same as when there was only the primary diagnosis.

The entry order of the diagnosis codes can impact the working DRG, especially the GMLOS. As previously mentioned, the primary diagnosis code should be listed first at the top diagnosis field. In FIGS. 8A and 8B, it can be seen how changing the order of the diagnosis entries impacts the working DRG, including changing the GMLOS from 2.4 to 3.6.

In FIG. 8A, the primary diagnosis is entered as "Acute on chronic systolic (congestive) heart failure" and the secondary diagnosis entry 802 is "Cardiac arrhythmia, unspecified." The diagnosis quality panel 830 has been auto-populated with data calculated specific to that diagnosis, including: DRG: 293 (803); Description: Heart failure & shock w/o CC/MCC (804); GMLOS: 2.4 (805); Weight: 0.6656 (806); APR DRG: 194 (807); APR DRG Description: Heart failure (808); and Severity of Illness: 1 (809); and Risk of Mortality: 1 (810).

In FIG. 8B, the order of the diagnosis entries has been reversed with "Cardiac arrhythmia, unspecified" entered in the primary diagnosis field 812 and "Acute on chronic systolic (congestive) heart failure" entered in the secondary diagnosis field 811. This change in position has had a significant effect on the data populated to the diagnosis quality panel 831. The details specific to the reversed diagnosis now show DRG: 308 (813); Description: Cardiac arrhythmia and conduction disorders w MCC (814); GMLOS: 3.6 (815); Weight: 1.2036 (816); APR DRG: 201 (817); APR DRG Description: Cardiac arrhythmia and conduction disorders (818); and Severity of Illness: 1 (819); and Risk of Mortality: 2 (820).

Entering Cardiac arrhythmia as the primary diagnosis has a significant effect on the data calculated for the diagnosis quality panel. The GMLOS is now 3.6 days instead of 2.4, the DRG weight has increased from 0.6656 to 1.2036, and the risk of mortality rating has increased from 1 (minor) to 2 (moderate). Proper ordering of the diagnosis codes allows the hospital to have a more accurate prediction of the time and resources that will be needed for treatment.

Figure 8C:
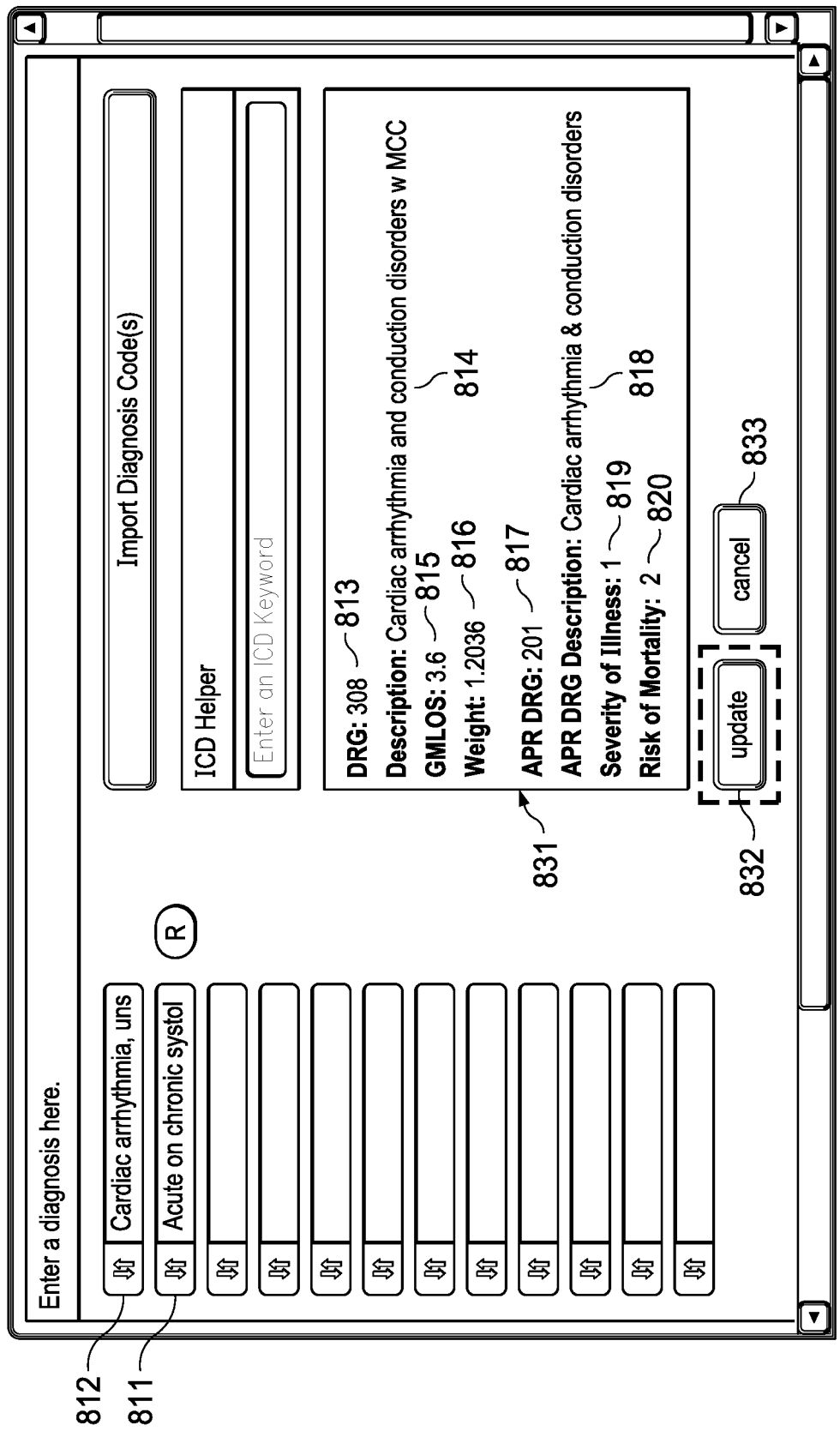
FIG. 8C shows the diagnosis screen with the updated button highlighted.

In FIG. 8C, the update button 832 is highlighted and actuating the button will update the system with the one or more selected diagnosis and the associated details calculated for the diagnosis. Alternatively, pressing the cancel button 833, will remove the entered diagnoses.

As the diagnosis codes are entered, the working DRG details are updated and displayed in the working DRG quality panel as well as the diagnosis quality panel. The diagnosis entered and relevant data calculated from the diagnosis is made available on the system in real-time to facilitate efficiency of care for the patient and accurate coding for the hospital. As shown in FIG. 9, the diagnosis order shown in FIG. 8B has been maintained with "Cardiac arrhythmia" entered in the primary diagnosis field 901 and "Acute on chronic systolic (congestive) heart failure" is entered in the secondary diagnosis field 902. The diagnosis quality panel 903 has the details as shown in FIG. 8B. The system now displays relevant working DRG data to the provider in multiple locations on the main screen for quick reference.

As seen in FIG. 9, the patient census bar 905 and the quality panel 910 have been updated to reflect the diagnosis related data calculated from the diagnoses entered in the diagnosis entry screen. The patient data display 909 in the quality panel 910 now displays a Working Diagnosis ((W) DRG) of "Cardiac arrhythmia & conduction disorders with MCC" properly reflecting the diagnoses entered in the diagnosis entry screen. The patient census bar 905 shows the 3.6 GMLOS (907) calculated for the working diagnosis.

The GMLOS 904 displayed in the diagnosis quality panel 903, is now also shown in the GMLOS field 907 of the patient census bar 905 at the top of page, and in the LOS/GMLOS navigation bar 914 in the quality panel 910. The LOS: 0 (906), GMLOS: 3.6 (907) and variance: −3.6 (908) shown under the patient census bar 905 is also displayed as 0/3.6 in the LOS/GMLOS navigation bar (914) and as −3.6 in the variance navigation bar (915). The LOS is presently shows as 0 and the Variance shows as −3.6 because the diagnosis has just been entered and no hospital days have passed yet. The LOS will increase for each inpatient day for the patient and variance will change to reflect the day has been used. Optionally, the variance can be shown combined with the LOS/GMLOS navigation bar to present the data as LOS/GMLOS/Variance, as seen in FIG. 3B. Displaying the data in multiple locations allows the User to view the data not only in in the diagnosis screen during diagnosis entry, but also in the patient's quality panel 910 and on the patient census bar 905 after the patient's quality panel has been collapsed.

The SOI and ROM ratings from the diagnosis quality panel 903 are now also presented as a SOI/ROM rating of ½ in the navigation bar (916). The DRG weight of 1.2036 seen in the diagnosis quality panel 903 is now also shown in the navigation bar 917, and "Edit diagnosis" is shown in the Diagnosis navigation bar 918 indicating a diagnosis has been entered. The missing charges navigation bar 920 indicates an alert because the patient entry and diagnosis is new and no charges have been posted.

As seen in FIG. 10, the provider also has easy access to a patient's RAF (Risk Adjustment Factor) and HCC (Hierarchical Condition Category). The RAF/HCC navigation bar 1019 shows the RAF/HCC rating as 1, and clicking the RAF/HCC navigation bar 1019 on the quality panel 1010 opens a RAF screen 1021 displaying the Risk Adjusted Diagnosis codes YTD for the selected patient, including the ICD code, HCC category, first recording physician and last recorded date.

As seen in FIG. 11, Clicking on the patient's name collapses the patient's record and the quality panel back to a patient census bar listing 1101. The patient census bar shows the LOS, GMLOS and Variance (1102) for each patient in the User's census listing. The LOS/GMLOS data 1103 for a second patient on the census list shows the LOS is 2 and the GMLOS is 4.2, indicating that 2 days of the 4.2 days projected have passed. The 2.2 Variance indicates that 2.2 days remain in the projected length of stay for that patient.

When data has been captured by the claimed system and method, the data can be analyzed by facility, date, patient, provider, diagnosis or other data entry. Working DRG reports can be generated on-demand by a user or generated automatically on a set scheduled basis, such as, daily, weekly, monthly, etc. Reports can be generated by operators or managers for the facility, as well as by the physicians.

To generate a report from data entered at the Working Diagnosis entry screen, the user accesses the analytics section of the Hospital Information System and can choose a report type from a report library to generate a report for the selected diagnosis related data points. Reports can be generated on selected combinations of data entries, including, but not limited to facility, physician, date range, diagnosis, or other data selection, as well as combinations of data types. The results can be reviewed and reported to the management team and the physicians. Analysis of the each of the elements provides data that can be used to improve diagnosis entries to more accurately project the required resources to ensure excellence in patient care.

The invention claimed is:

1. A method comprising the steps of:
   entering, via a diagnosis entry subprogram on a hardware data processor patient system, one or more diagnosis for a patient in a health care setting, said one or more diagnosis being a primary diagnosis, and one or more of a secondary diagnosis, a complication diagnosis, or a comorbidity diagnosis;
   inputting a description of the diagnosis into the diagnosis entry subprogram by:
      entering, via the diagnosis entry subprogram on the hardware data processor patient system, a diagnosis description by manual entry, or
      selecting, via the diagnosis entry subprogram on the hardware data processor patient system, a diagnosis description from a menu, or
      importing, via the diagnosis entry subprogram on the hardware data processor patient system, a diagnosis description from an external source, or
      entering, via the diagnosis entry subprogram on the hardware data processor patient system, an International Classification of Disease (ICD) number, for each of said one or more diagnosis;
   analyzing, via the diagnosis entry subprogram on the hardware data processor patient system, said one or more diagnosis in view of the patient's age and sex, discharge status, and any surgical procedures previously performed on said patient;
   calculating, via the diagnosis entry subprogram on the hardware data processor patient system, diagnosis specific data that includes at least one Diagnosis Related Grouping (DRG) code wherein the diagnosis specific data is calculated based on how said one or more diagnosis was entered in said diagnosis entry subprogram;
   generating, via the diagnosis entry subprogram on the hardware data processor patient system, a working diagnosis from the diagnosis specific data calculated by the diagnosis entry subprogram;
   populating one or more display fields of an electronic medical record (EMR) with the working diagnosis and at least one DRG code generated by the diagnosis entry subprogram,
   displaying the working diagnosis and at least some of said diagnosis specific data calculated by said diagnosis entry subprogram; and
   storing said one or more diagnosis specific data and said working diagnosis generated by said diagnosis entry subprogram in said plurality of non-transitory storage devices programmed with executable instructions using said hardware data processor patient system.

2. The method of claim 1, further comprising:
   calculating one or more modified diagnosis specific data when one or more modified diagnosis is entered via the diagnosis entry subprogram on the hardware data processor patient system, said diagnosis specific data including at least one Diagnosis Related Grouping (DRG) code, and one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating;
   generating a modified working diagnosis from the modified diagnosis specific data calculated by the diagnosis entry subprogram;
   populating one or more display field of the EMR with the modified diagnosis specific data;
   displaying the modified working diagnosis and the modified diagnosis specific data; and
   storing said one or more modified diagnosis, said one or more modified diagnosis specific data, and said modified working diagnosis in plurality of non-transitory storage devices programmed with executable instructions using said hardware data processor patient system.

3. The method of claim 1, wherein said diagnosis specific data further comprises one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating.

4. The method of claim 3, wherein said one or more display field of the EMR is populated with the working diagnosis, the DRG code, and one or more of Diagnosis description, DRG weight, LOS, GMLOS, APR DRG, APR DRG Description, LOS/GMLOS/Variance rating, SOI/ROM, diagnosis status, and RAF/HCC rating.

5. The method of claim 4, wherein the one or more display field of the EMR is one or more display field of a diagnosis quality panel, one or more display field of a patient quality panel, one or more display field of a patient census bar, or combinations thereof.

6. The method of claim 2, wherein said one or more display field of the EMR is one or more display field of the diagnosis quality panel, one or more display field of the patient quality panel, one or more display field of the patient census bar, or combinations thereof.

7. The method of claim 1, wherein one or more selectable options are displayed in a dropdown menu when two are more letters are manually input into the diagnosis field.

8. The method of claim 1, wherein the EMR shows alerts for missing data, said alert being an alert icon, a change in color, or a combination thereof.

9. The method of claim 1, wherein the EMR displays color coding, bold text, a leading letter designation, or combinations thereof, with entries for Major Complication or Comorbidity/Complication or Comorbidity (MCC/CC), and risk adjusted diagnoses for rapid visual identification.

10. The method of claim 1, wherein the diagnosis entry subprogram has customizable abbreviations for DRG codes.

11. A method comprising the steps of:
entering, via a diagnosis entry subprogram on a hardware data processor patient system, one or more diagnosis for a patient in a health care setting,
inputting a description of the diagnosis into the diagnosis entry subprogram by:
  entering, via the diagnosis entry subprogram on the hardware data processor patient system, a diagnosis description, by manual entry, or
  selecting, via the diagnosis entry subprogram on the hardware data processor patient system, a diagnosis description from a menu, or
  importing, via the diagnosis entry subprogram on the hardware data processor patient system, a diagnosis description from an external source, or
  entering, via the diagnosis entry subprogram on the hardware data processor patient system, an International Classification of Disease (ICD) number, for each of said one or more diagnosis;
analyzing, via said diagnosis entry subprogram on the hardware data processor patient system, the diagnosis entered therein in view of the patient's age and sex, discharge status, and any surgical procedures performed;
calculating, via the diagnosis entry subprogram on the hardware data processor patient system, diagnosis specific data that includes at least one Diagnosis Related Grouping (DRG) code wherein the diagnosis specific data is calculated based on how said diagnosis is entered in said diagnosis entry subprogram;
generating, via the diagnosis entry subprogram on the hardware data processor patient system, a working diagnosis from the diagnosis specific data calculated by the subprogram;
populating one or more display fields of an electronic medical record (EMR) with the working diagnosis and at least some of said diagnosis specific data generated by the diagnosis entry subprogram,
displaying the working diagnosis and one or more diagnosis specific data generated from said diagnosis entered therein; and
storing said one or more diagnosis specific data and said working diagnosis generated by said diagnosis entry subprogram in one or more of said plurality of non-transitory storage devices programmed with executable instructions using said hardware data processor patient system.

12. The method of claim 11, further comprising:
calculating one or more modified diagnosis specific data when one or more modified diagnosis is entered via the diagnosis entry subprogram on the hardware data processor patient system, said diagnosis specific data including at least one Diagnosis Related Grouping (DRG) code, and one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating;
generating a modified working diagnosis from the modified diagnosis specific data calculated by the diagnosis entry subprogram;
populating one or more display field of the EMR with the modified diagnosis specific data;
displaying the modified working diagnosis and one or more modified diagnosis specific data; and
storing said one or more modified diagnosis, said one or more modified diagnosis specific data, and said modified working diagnosis in said plurality of non-transitory storage devices programmed with executable instructions using said hardware data processor patient system.

13. The method of claim 11, wherein said one or more diagnosis is a primary diagnosis, one or more secondary diagnosis, one or more complication diagnosis, one or more comorbidity diagnosis, or combinations thereof, said one or more diagnosis comprising at least one primary diagnosis.

14. The method of claim 11, wherein one or more selectable options are displayed in a dropdown menu when two are more letters are manually input into the diagnosis field.

15. The method of claim 11, wherein said diagnosis specific data includes at least one Diagnosis Related Grouping (DRG) code, and one or more of DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating.

16. The method of claim 11, wherein said one or more display field of the EMR is one or more display fields of a diagnosis quality panel, one or more display fields of a patient quality panel, one or more display field of a patient census bar, or combinations thereof.

17. The method of claim 12, wherein said one or more display field of the EMR is one or more display fields of the diagnosis quality panel, one or more display fields of the patient quality panel, one or more display field of the patient census bar, or combinations thereof.

18. The method of claim 11, wherein said one or more display field of said EMR shows alerts for missing data said alert being an alert icon, a change in color, or a combination thereof.

19. The method of claim 11, wherein said one or more display field of said EMR displays color coding, bold text, a leading letter designation, or combinations thereof, with entries for Major Complication or Comorbidity/Complication or Comorbidity (MCC/CC), and risk adjusted diagnoses for rapid visual identification.

20. A method comprising the steps of:

entering, via a diagnosis entry subprogram on a hardware data processor patient system, one or more diagnosis for a patient in a health care setting, said one or more diagnosis being at least a primary diagnosis;

inputting a description of the diagnosis into the diagnosis entry subprogram by:

entering, via the diagnosis entry subprogram on the hardware data processor patient system, a diagnosis description by manual entry, or selecting, via the diagnosis entry subprogram on the hardware data processor patient system, a diagnosis description from a menu, or importing, via the diagnosis entry subprogram on the hardware data processor patient system, a diagnosis description from an external source, or entering, via the diagnosis entry subprogram on the hardware data processor patient system, an International Classification of Disease (ICD) number, for each of said one or more diagnosis;

analyzing, via the diagnosis entry subprogram on the hardware data processor patient system, the diagnosis entered into said diagnosis entry subprogram in view of the patient's age and sex, discharge status, and any surgical procedures previously performed on said patient;

calculating, via the diagnosis entry subprogram on the hardware data processor patient system, diagnosis specific data that includes at least one Diagnosis Related Grouping (DRG) code, wherein the diagnosis specific data is calculated based on how said one or more diagnosis was entered into the diagnosis entry subprogram;

generating, via the diagnosis entry subprogram on the hardware data processor patient system, a working diagnosis from the diagnosis specific data calculated by the diagnosis entry subprogram;

displaying the working diagnosis and one or more diagnosis specific data generated from said diagnosis data entered therein; and storing said one or more diagnosis specific data and said working diagnosis generated by said diagnosis entry subprogram, in said plurality of non-transitory storage devices programmed with executable instructions using said hardware data processor patient system.

21. The method of claim 20, further comprising:

calculating one or more modified diagnosis specific data when one or more modified diagnosis is entered via the diagnosis entry subprogram on the hardware data processor patient system, said diagnosis specific data including at least one Diagnosis Related Grouping (DRG) code, and one or more of a DRG weight, Length of Stay (LOS), Geometric Mean Length of Stay (GMLOS), All Patients Refined (APR) DRG code, APR DRG Description, LOS/GMLOS/Variance rating, Severity of Illness/Risk of Mortality (SOI/ROM), diagnosis status, and Risk Adjusted Factor/Hierarchical Condition Category (RAF/HCC) rating;

generating a modified working diagnosis from the modified diagnosis specific data calculated by the diagnosis entry subprogram;

populating one or more display field of the EMR with one or more of the modified diagnosis specific data; the modified working diagnosis, or combinations thereof;

displaying the modified working diagnosis and one or more of the modified diagnosis specific data; and storing said one or more modified diagnosis, said one or more modified diagnosis specific data, and said modified working diagnosis in plurality of non-transitory storage devices programmed with executable instructions using said hardware data processor patient system.

22. The method of claim 20, wherein said diagnosis further includes one or more secondary diagnosis, one or more complication diagnosis, one or more comorbidity diagnosis, or combinations thereof.

23. The method of claim 20, wherein one or more selectable options are displayed in a dropdown menu when two are more letters are manually input into the diagnosis field.

24. The method of claim 20, further comprising populating one or more fields of a patient census bar of the EMR with one or more of said working diagnosis, DRG code, Diagnosis description, DRG weight, GMLOS, APR DRG, APR DRG Description, LOS/GMLOS/Variance rating, SOI/ROM, Diagnosis status, and RAF/HCC rating.

25. The method of claim 20, wherein said one or more display field of the EMR shows alerts for missing data, said alert being an alert icon, a change in color, or a combination thereof.

26. The method of claim 20, wherein said one or more display field of the EMR displays color coding, bold text, a leading letter designation, or a combination thereof, with entries for Major Complication or Comorbidity/Complication or Comorbidity (MCC/CC), and risk adjusted diagnoses for rapid visual identification.

27. The method of claim 20, wherein said one or more display field of the EMR is one or more display field of the diagnosis quality panel, one or more display field of the patient quality panel, one or more display field of the patient census bar, or combinations thereof.

* * * * *

UNITED STATES PATENT AND TRADEMARK OFFICE
CERTIFICATE OF CORRECTION

| | |
|---|---|
| PATENT NO. | : 12,080,431 B1 |
| APPLICATION NO. | : 17/735847 |
| DATED | : September 3, 2024 |
| INVENTOR(S) | : Merced Gonzales, Jr. |

Page 1 of 1

It is certified that error appears in the above-identified patent and that said Letters Patent is hereby corrected as shown below:

In the Claims

Column 30 Line 53 Claim 2, before "plurality" insert --said--
Column 31 Line 15 Claim 7, after "two" delete "are" and insert --or--
Column 32 Line 40 Claim 14, after "two" delete "are" and insert --or--
Column 34 Line 19 Claim 21, before "plurality" insert --said--
Column 34 Line 29 Claim 23, after "two" delete "are" and insert --or--

Signed and Sealed this
Fifth Day of November, 2024

Katherine Kelly Vidal
*Director of the United States Patent and Trademark Office*